US011918696B2

United States Patent
Nath et al.

(10) Patent No.: US 11,918,696 B2
(45) Date of Patent: Mar. 5, 2024

(54) SAFETY CABINET WITH ILLUMINATION SYSTEM

(71) Applicant: Justrite Manufacturing Company LLC, Deerfield, IL (US)

(72) Inventors: Keshar Nath, Wilton, CT (US); Mark Goddard, Charleston, IL (US)

(73) Assignee: Justrite Manufacturing Company, LLC, Deerfield, IL (US)

( * ) Notice: Subject to any disclaimer, the term of this patent is extended or adjusted under 35 U.S.C. 154(b) by 0 days.

(21) Appl. No.: 17/170,180

(22) Filed: Feb. 8, 2021

(65) Prior Publication Data
US 2022/0143235 A1 May 12, 2022

Related U.S. Application Data

(60) Provisional application No. 63/111,609, filed on Nov. 9, 2020.

(51) Int. Cl.
*A61L 2/10* (2006.01)
*F21S 4/24* (2016.01)
(Continued)

(52) U.S. Cl.
CPC . *A61L 2/10* (2013.01); *F21S 4/24* (2016.01); *F21V 33/0012* (2013.01);
(Continued)

(58) Field of Classification Search
CPC ........ H01B 17/30; H01J 5/32; A61L 2202/11; A61L 2/10; F21V 33/0068;
(Continued)

(56) References Cited

U.S. PATENT DOCUMENTS 2,672,500 A * 3/1954 Bondon ............... H01B 17/306
439/271
5,160,699 A * 11/1992 Siegal ..................... A61L 2/10
250/455.11
(Continued)

FOREIGN PATENT DOCUMENTS

| CN | 208003132 U | 10/2018 |
| GB | 2368001 A | 4/2002 |

OTHER PUBLICATIONS

European Patent Office, International Search Report and Written Opinion of the International Search Authority in International Patent Application No. PCT/US2021/058594 (dated Feb. 18, 2022).

*Primary Examiner* — Evan P Dzierzynski
*Assistant Examiner* — Nathaniel J Lee
(74) *Attorney, Agent, or Firm* — Leydig, Voit & Mayer, Ltd.

(57) ABSTRACT

A safety cabinet can include an enclosure defining an interior compartment accessible through an opening. The safety cabinet includes an interior lighting system. The interior lighting system can include at least one of an illuminating light to enable viewing to cabinet contents and an ultraviolet light configured to disinfect the interior compartment of the safety cabinet. To provide electrical power to the interior lighting system, the safety cabinet includes an electrical connection disposed through the enclosure. The electrical connection can include at least one of a bulkhead connector and an intumescent socket.

21 Claims, 16 Drawing Sheets

(51) Int. Cl.
*F21V 33/00* (2006.01)
*F21W 131/301* (2006.01)
*F21Y 115/10* (2016.01)

(52) U.S. Cl.
CPC ........ *A61L 2202/11* (2013.01); *A61L 2202/23* (2013.01); *F21W 2131/301* (2013.01); *F21Y 2115/10* (2016.08)

(58) Field of Classification Search
CPC .............. F21V 33/0012; B08B 7/0057; F21Y 2115/10; F21S 4/24; E05Y 2900/21
See application file for complete search history.

(56) References Cited

U.S. PATENT DOCUMENTS

| | | | |
|---|---|---|---|
| 6,729,701 B2 | 5/2004 | Carter et al. | |
| 8,172,344 B2 | 5/2012 | Eyer et al. | |
| 8,240,872 B1 | 8/2012 | Horn | |
| 8,473,097 B2 | 6/2013 | Shoenfeld | |
| 9,630,036 B2 | 4/2017 | Strum et al. | |
| 2006/0263275 A1* | 11/2006 | Lobach | B01L 1/00 422/186 |
| 2009/0091220 A1 | 4/2009 | Eyer et al. | |
| 2011/0243789 A1* | 10/2011 | Roberts | A61L 2/10 422/116 |
| 2011/0273867 A1 | 11/2011 | Horst et al. | |
| 2012/0051030 A1* | 3/2012 | Johnson | F25D 17/042 362/92 |
| 2013/0021811 A1* | 1/2013 | Goldwater | B62J 6/01 362/249.04 |
| 2013/0200767 A1* | 8/2013 | Mueller | A47B 96/00 312/295 |

\* cited by examiner

SAFETY CABINET WITH ILLUMINATION SYSTEM

CROSS-REFERENCE TO RELATED APPLICATIONS

This patent application claims the benefit of priority to U.S. Provisional Patent Application No. 63/111,609, filed Nov. 9, 2020, and entitled, "Safety Cabinet with Illumination System," which is incorporated in its entirety herein by this reference.

TECHNICAL FIELD

This patent disclosure relates generally to a safety cabinet and, more particularly, to a safety cabinet including an interior lighting system.

BACKGROUND

Safety cabinets are often used to safely store hazardous and/or flammable materials at an onsite facility such as a plant, factory, or laboratory. Safety cabinets are constructed to provide an interior compartment to accommodate the subject materials in isolation from the ambient surroundings so that spillage or ignition of the material is contained in the safety cabinet and so that the materials stored in the safety cabinet are protected from external ignition sources. Due to their protective importance, safety cabinets are often designed to comply with one or more regulatory guidelines or requirements such as those promulgated by the Occupational Safety and Health Administration (OSHA) and the National Fire Protection Association (NFPA). An "FM Approval" is a type of third party testing and certification service performed by FM Global that is given to products like safety cabinets as capable of withstanding and limiting the effects of fires and explosions based upon certain standardized tests.

Safety cabinets typically include an enclosure that defines the interior compartment for accommodating the hazardous and/or flammable materials. One or more shelves may be disposed in the interior compartment for supporting the materials, which may be contained in packaging such as jars, boxes, or safety cans, for example. One or more doors may selectively close access to the interior compartment of the safety cabinet.

There is a continued need in the art to provide additional solutions to enhance the convenient use of the safety cabinet. For example, there is a continued need for techniques for helping a user identify the contents stored within a safety cabinet.

It will be appreciated that this background description has been created by the inventors to aid the reader, and is not to be taken as an indication that any of the indicated problems were themselves appreciated in the art. While the described principles can, in some aspects and embodiments, alleviate the problems inherent in other systems, it will be appreciated that the scope of the protected innovation is defined by the attached claims, and not by the ability of any disclosed feature to solve any specific problem noted herein.

SUMMARY

The present disclosure, in one aspect, is directed to embodiments of a safety cabinet. In embodiments, the safety cabinet includes an interior lighting system. In some of such embodiments, a safety cabinet includes an interior lighting system having at least one ultraviolet light source configured to selectively disinfect an interior of the safety cabinet. In at least some of such embodiments, a safety cabinet includes an interior lighting system having at least one light emitting diode ("LED") disposed in an interior compartment of the safety cabinet to illuminate the interior compartment and the contents stored therein.

In another aspect, to provide electric power for the interior lighting system, the disclosure provides embodiments of an electrical connection disposed through an enclosure of a safety cabinet in a manner that maintains selective isolation of the interior compartment. The electrical connection can be configured to maintain compliance with safety regulations such as FM approval.

In one embodiment, a safety cabinet includes an enclosure, a door, an interior lighting system, and an electrical connection. The enclosure defines an interior compartment and a compartment opening. The interior compartment is accessible via the compartment opening. The door is rotatably mounted to the enclosure and moveable over a range of travel between an open position and a closed position. The door is adapted to cover at least a portion of the compartment opening of the enclosure when the door is in the closed position. The interior lighting system includes at least one light source disposed in the interior compartment. The electrical connection is conductively connected to the interior lighting system. The electrical connection is arranged with the enclosure and configured to be electrically connected to an external electrical component such that the interior compartment is isolated from an exterior environment via the electrical connection.

In still another aspect of the present disclosure, embodiments of a method of disinfecting a safety cabinet are disclosed. In embodiments, a method of disinfecting a safety cabinet includes activating for a predetermined period of time an interior lighting system that includes an ultraviolet light source disposed in an interior compartment of the safety cabinet.

In an embodiment, a method of disinfecting an interior compartment of a safety cabinet can be used in which the safety cabinet includes an enclosure and at least one door. The enclosure includes an inner shell and an outer shell in a double walled configuration. The inner shell defines an interior compartment and a compartment opening. The interior compartment is accessible via the compartment opening, and the at least one door is rotatably mounted to the enclosure and moveable over a range of travel between an open position and a closed position. The at least one door is adapted to occlude the compartment opening of the enclosure when the at least one door is in the closed position. The method includes electrically connecting an interior lighting system disposed in the interior compartment to an external electrical component via an electrical connection disposed through the inner shell and the outer shell of the enclosure and configured to isolate the interior compartment from an exterior environment. The compartment opening is occluded by moving each of the at least one door to the closed position. At least one ultraviolet light source of the interior lighting system is activated for a predetermined period of time sufficient to reduce at least one of a microorganism and a pathogen disposed within the interior compartment.

Further and alternative aspects and features of the disclosed principles will be appreciated from the following detailed description and the accompanying drawings. As will be appreciated, the safety cabinets and methods disclosed herein are capable of being carried out in other and different embodiments, and capable of being modified in various respects. Accordingly, it is to be understood that both the foregoing general description and the following detailed description are exemplary and explanatory only and do not restrict the scope of the appended claims.

Figure 1:
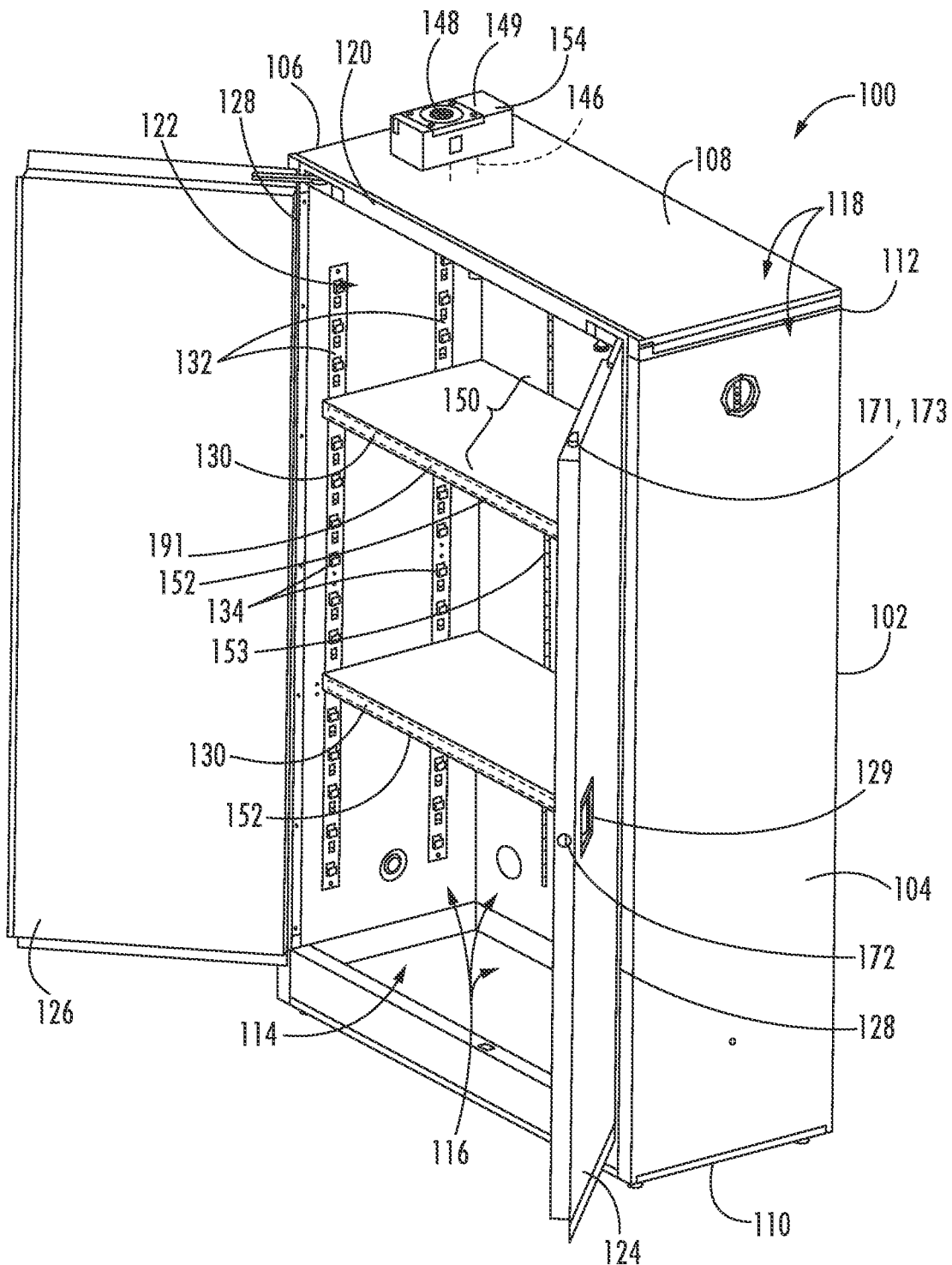
FIG. 1 is a front perspective view of an embodiment of a safety cabinet constructed in accordance with principles of the present disclosure, the safety cabinet including an embodiment of an interior lighting system constructed in accordance with principles of the present disclosure for illuminating an interior compartment for accommodating hazardous or flammable materials and that is constructed in compliance with one or more safety regulations.

It should be understood that the drawings are not necessarily to scale and that the disclosed embodiments are illustrated diagrammatically and in partial views. In certain instances, details which are not necessary for an understanding of this disclosure or which render other details difficult to perceive may have been omitted. It should be understood that this disclosure is not limited to the particular embodiments illustrated herein.

DETAILED DESCRIPTION OF EXEMPLARY EMBODIMENTS

Aspects of the present disclosure are directed to embodiments of a safety cabinet configured to help enable users to clearly see the contents of the safety cabinet, for example, by inclusion of an interior lighting system. Aspects of the present disclosure are directed to embodiments of a safety cabinet configured to establish an electrical connection to the interior compartment through the enclosure to provide electrical power to the interior lighting system while maintaining compliance with safety regulations and guidelines such as FM approvals.

Now referring to the drawings, wherein like reference numbers refer to like elements, there is illustrated in FIGS. 1-5 an exemplary embodiment of a safety cabinet 100 constructed in accordance with the disclosure for accommodating hazardous and/or flammable materials. The safety cabinet 100 illustrated in FIG. 1 has a generally vertical configuration in that it stands upright and is accessible through the forward face; in other embodiments the safety cabinet may have a relatively low, horizontal configuration and may be accessible through the top. In the embodiment illustrated in FIG. 1, the safety cabinet 100 can include a rear wall 102, a first sidewall 104 and a second sidewall 106 that are joined to and extend perpendicularly from the rear wall 102 such that the first and second sidewalls 104, 106 are parallel to each other. The safety cabinet 100 can also include a top or ceiling 108 and a lower bottom or floor 110 that are joined to, and perpendicular with respect to, the rear wall 102, the first sidewall 104, and the second sidewall 106. The rear wall 102 and the first and second sidewalls 104, 106 are oriented vertically and stand upright while the top 108 and the bottom 110 are oriented horizontally, so the safety cabinet 100 has a substantially rectangular shape; however, it should be appreciated that the terms "vertical," "horizontal," "top," "bottom," and the like are for reference purposes only and are not limitations on the disclosure. In addition, the safety cabinet 100 can include additional or non-planar walls to provide different shapes and configurations. The rear wall 102, the first and second sidewalls 104, 106, the top 108, and the bottom 110 can be made of a suitable, fire resistant material such as steel or aluminum, although other structural materials may be used and are within the scope of the disclosure.

The rear wall 102, the first and second sidewalls 104, 106, the top 108, and the bottom 110 provide an enclosure 112 that defines a hollow interior compartment 114. The rear wall 102, the first and second sidewalls 104, 106, the top 108 and the bottom 110 may be flat and relatively planar. The rear wall 102, the first and second sidewalls 104, 106, the top 108 and the bottom 110 can be connected together by any suitable technique, as will be appreciated by one skilled in the art, such by being fixedly joined with fasteners such as bolts or screws, welded together, or joined by adhesives. Fixedly joining the rear wall 102, the first and second sidewalls 104, 106, the top 108 and the bottom 110 together provides a rigid, durable structure that corresponds to the enclosure 112.

The illustrated safety cabinet 100 has a double-walled construction. In particular, each component of the enclosure 112 has a double-walled construction. Referring to FIG. 1, the enclosure 112 includes an inner shell 116 and an outer shell 118 to provide a double-walled construction, wherein each outer wall of the outer shell 118 has a corresponding inner wall of the inner shell 116, with the corresponding inner and the outer walls separated by a predetermined distance to define an insulative air space.

Figure 5:
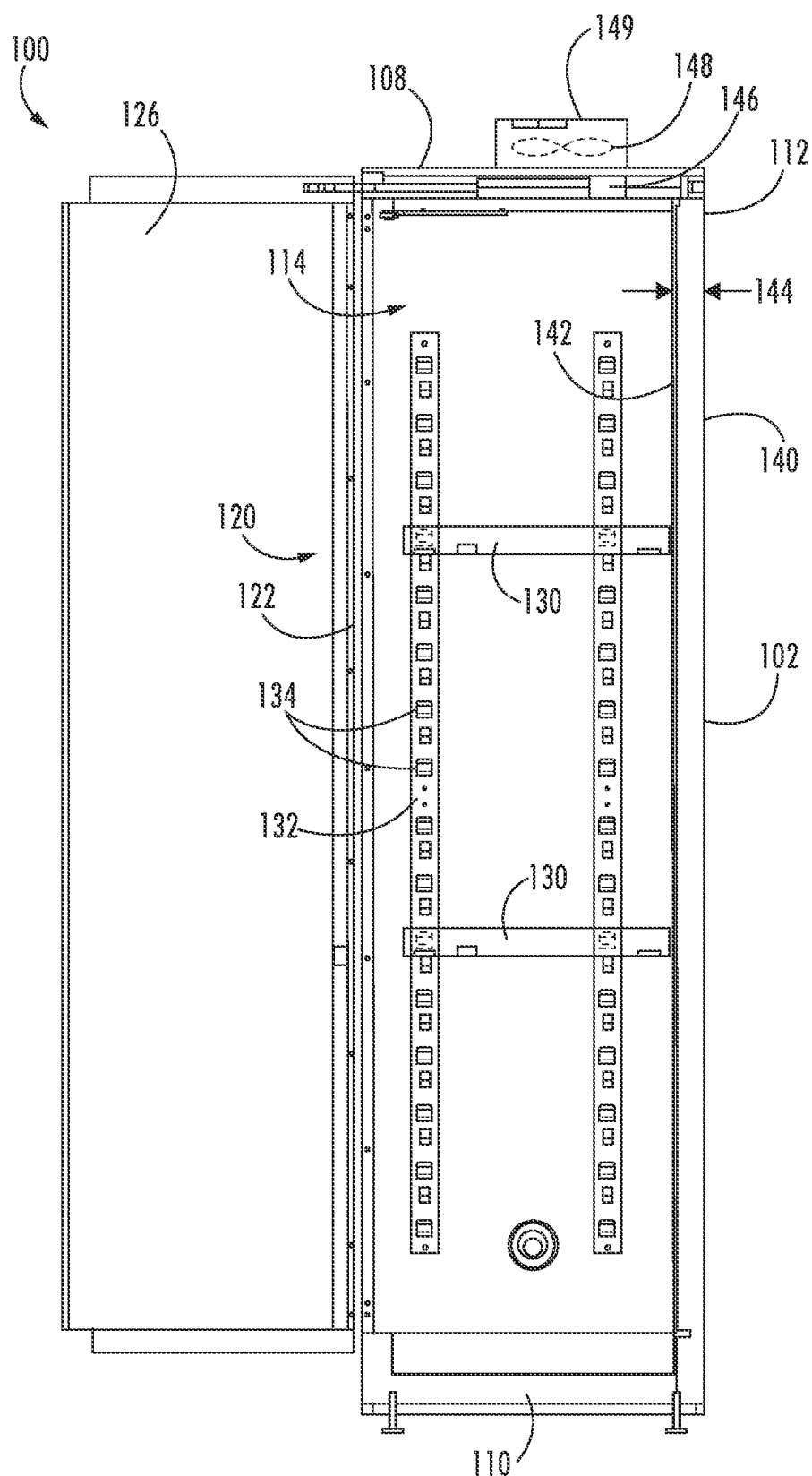
FIG. 5 is a cross-sectional view of the safety cabinet taken along line 5-5 of FIG. 4 that shows the double panel construction of the rear wall of the enclosure and a pair of shelf uprights configured to support the plurality of shelves.

For example, referring to FIG. 5, the rear wall 102 may be formed of an internal panel 140 and an external panel 142 that are planar, arranged parallel to each other, and are spaced apart from each other to define an air gap 144 there between. The first and second sidewalls 104, 106, the top 108, and the bottom 110 may have a similar double panel construction that defines an air gap 144 between internal and external panels 140, 144. The air gap 144 can resist the thermal transfer of heat between the internal panel 140 and the external panel 142. In embodiments, heat or fire resistant insulation may be disposed between the internal panel 140 and the external panel 142. Additionally, to further seal the interior compartment 114, a compressive seal made of rubber, foam, or a similar compressible material can be disposed on the forward frame 120 that the first and second doors 124, 126 can press against when in the closed position.

To access the interior compartment 114, the forward edges of the first and second sidewalls 104, 106, the top 108, and the bottom 110 form a forward frame 120 that outlines a compartment opening 122 through which access to the interior compartment 114 of the safety cabinet 100 is provided. The forward frame 120, and the corresponding compartment opening 122 defined by the forward frame 120, can be rectangular although other shapes and outlines are contemplated in other embodiments. To close the compartment opening 122 and shut the interior compartment 114, a first door 124 and a second door 126 may be pivotally attached to the forward frame 120 by one or more hinges 128. The hinges 128 can be a continuous hinge that runs along a major portion of the height of the respective door 124, 126 to which it is attached. In other embodiments, a plurality of discrete hinges can be provided along the height of the respective door 124, 126 rather than the continuous, "piano" style hinges 128 illustrated in FIG. 1. Additionally, while the doors 124, 126 and the hinges 128 have a rotational axis that is vertically oriented, in other embodiments, the rotational axis may be aligned horizontally.

When in the closed position, the first and second doors 124, 126 are parallel to and spaced apart from the rear wall 102. In an embodiment, to securely contain the contents of the safety cabinet, the first and second doors 124, 126 can include door handles 129 that are operatively associated with a locking mechanism that may operatively interact with the forward frame 120 via sliding dead bolts or the like to prevent unintended opening of the interior compartment 114.

In embodiments, the safety cabinet 100 can include any suitable latch system 171 adapted to help retain the doors 124, 126 in the closed position. In embodiments, the latch system 171 can be a three-point latch system having various configurations, including a slam-latch style that need not be operated in order to permit the doors 124, 126 to move from an open position to the closed position. In embodiments, the latch system 171 includes a bullet slam latch 172, first and second latch rod assemblies 173, 174 (see FIG. 3), and the paddle handle 129. In embodiments, the first and second latch rod assemblies each includes a distal bullet slam latch as described in U.S. Pat. No. 9,630,036, which is incorporated herein by reference. The paddle handle 129 is adapted to selectively actuate the latch system 171 to move the distal ends of the latch rod assemblies 173, 174 and the bullet slam latch 172 from an extended position to a retracted position in which the doors 124, 126 can be moved from the closed position to one of a range of open positions. The bullet slam latch 172 and the first and second latch rod assemblies 173, 174 are adapted to bias the latch members to extended positions but also to permit the latch members to move from the extended positions to respective retracted positions in response to the door 124 moving from an open position to the closed position (in other words, when it is "slammed" closed).

Figure 6:
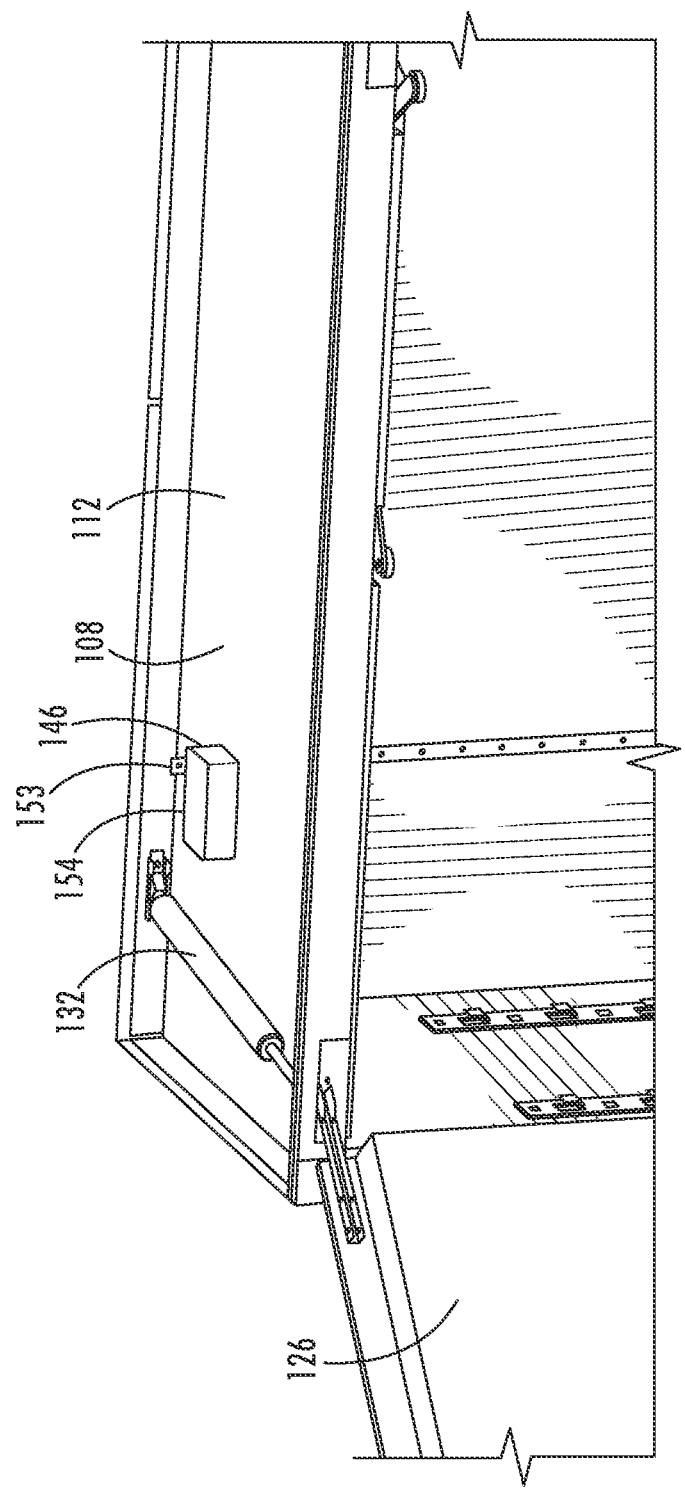
FIG. 6 is a fragmentary, perspective view of a top of the safety cabinet of FIG. 1 with a wall of the outer shell removed for illustrative purposes.

In some embodiments, the safety cabinet 100 can include means for automatically closing the doors. In embodiments, the safety cabinet 100 includes first and second actuators 131, 132 (see, e.g., FIG. 3) adapted to urge the first and second doors 124, 126, respectively, to the closed position. Referring to FIG. 6, in the illustrated embodiment, first and second actuators have the same construction (only the second actuator 132 is shown) and are in the form of hydraulic cylinders are attached to the first and second doors 124, 126, respectively, and to the enclosure 112. The hydraulic cylinders 131, 132 are adapted to bias the first and second doors 124, 126 to their closed positions.

While loading and unloading the safety cabinet 100, it may be desirable that the doors 124, 126 remain in an open position. In some embodiments, the safety cabinet 100 can include means for selectively retaining the doors 124, 126 in an open position. In embodiments, the means for selectively retaining the doors 124, 126 in an open position comprises a retaining system having the construction and functionality of the retaining system 42 described in U.S. Pat. No. 6,729,701, which is incorporated herein by this reference.

In embodiments, to create a more effective seal, the outer and inner sealing flanges of the first and second doors 124, 126 are arranged such that the inner sealing flange of the second door 126 is disposed in inward relationship to the first door 124, and the outer sealing flange of the first door 124 is disposed in outer relationship to the second door 126. In embodiments, a suitable sequential door-closing system 90 can be provided that is adapted to coordinate the closure of the doors 38, 40 such that the left door 38 closes before the right door 40. In embodiments, any suitable sequential door-closing system 90 can be used, such as the sequential door-closing system shown in FIG. 2 and further described in U.S. Patent Application Publication No. US2013/0200767, for example. In other embodiments, a sequential door-closing system constructed according to principles described in U.S. Pat. No. 6,729,701 can be used.

Referring to FIG. 1, to support the contents of the safety cabinet 100, one or more shelves 130 can be disposed in the interior compartment 114. The shelves 130 can be arranged horizontally and can extend between the first sidewall 104 and the second sidewall 106. In addition to the shelves 130, the bottom 110 may function as a lower base shelf onto which items can be set. In embodiments, to adjust the vertical elevation of the shelves 130, one or more upright supports 132 can be formed in or attached to the first and second sidewalls 104, 106 and can extend generally between the top 108 and the bottom 110. The upright supports 132 can include a plurality of vertically extending notches 134 that can accommodate clips or brackets on which the horizontal shelves 130 can rest. In embodiments, the safety cabinet 100 can include shelves and shelf mounts constructed according to principles described in U.S. Pat. No. 8,172,344, which is incorporated herein by this reference.

Referring to FIG. 1, to enable a user to see the contents of the safety cabinet 100, an interior lighting system 150 may be included with the safety cabinet to illuminate the interior compartment 114. In embodiments, the interior lighting system 150 can include at least one light source 152, a conductive strip 153, and a power supply 154. In embodiments, each light source 152 can have any suitable construction configured to emit light, and can include the associated fixtures, electrical connections, electrically conductive pathways, and other components like power convertors, switches and illumination or brightness controls for providing selective emission of light within the interior compartment 114 of the safety cabinet 100.

In embodiments, the plurality of light sources 152 can be physically and conductively connected together to facilitate attachment to the interior compartment 114. The light sources 152 may be removable and replaceable or may be a permanent part of the interior lighting system 150. Examples of light sources 152 suitable for use in embodiments of a lighting system 150 constructed according to principles of the present disclosure include those utilizing incandescent lights with filaments, halogen lights, light emitting diodes ("LEDs"), fluorescent or gas discharge lamps, or, in an embodiment described below, ultraviolet ("UV") lamps for disinfection purposes. The light emitted from the interior lighting system 150 may be white in color or may be another particular color of the spectrum.

Figure 7:
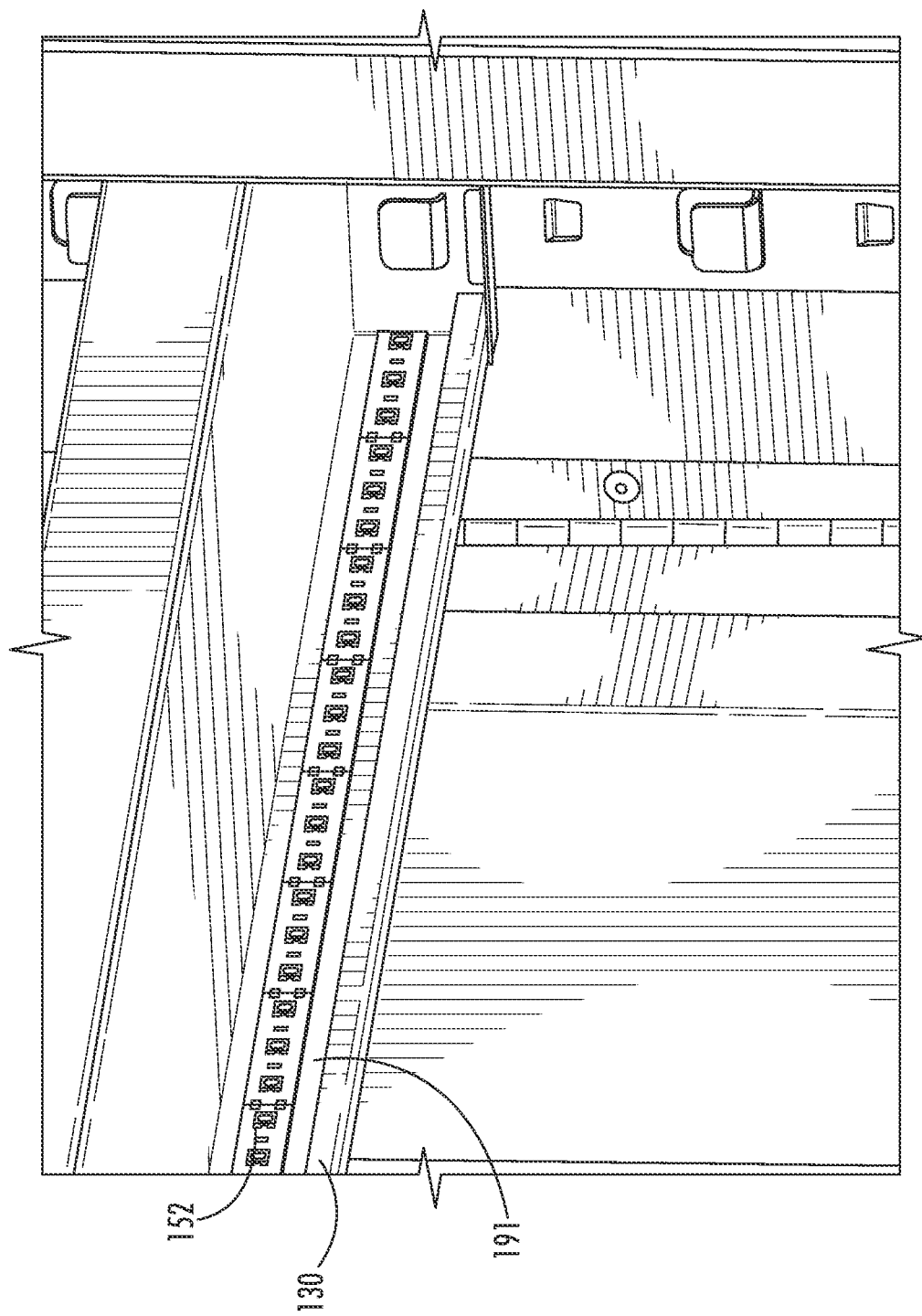
FIG. 7 is a fragmentary, perspective view of an inner side of a front lip of a shelf of the safety cabinet of FIG. 1, illustrating a light source of the interior lighting system in the form of an LED ribbon strip.

In the illustrated embodiment, each of the shelves 130 disposed within the safety cabinet 100 is equipped with one of the light sources 152 (see FIG. 7). Referring to FIGS. 1 and 7, the light source 152 is mounted to the inner side of a front lip 191 of the shelf 130 such that the light source 152 is positioned to emit light toward the rear wall 102 of the enclosure 112.

Referring to FIG. 1, in embodiments, the conductive strip 153 can comprise any suitable device for conveying electrical power within the interior compartment 114 of the safety cabinet 100 to each light source 152 of the interior lighting system. In the illustrated embodiment, the conductive strip 153 is mounted to the interior of the rear wall 102 of the safety cabinet 100. Referring to FIG. 6, the conductive strip 153 extends into the insulative air space of the top 108 and is electrically connected to the power supply 154 which is also disposed within the top 108 of the safety cabinet 100.

Figure 8:
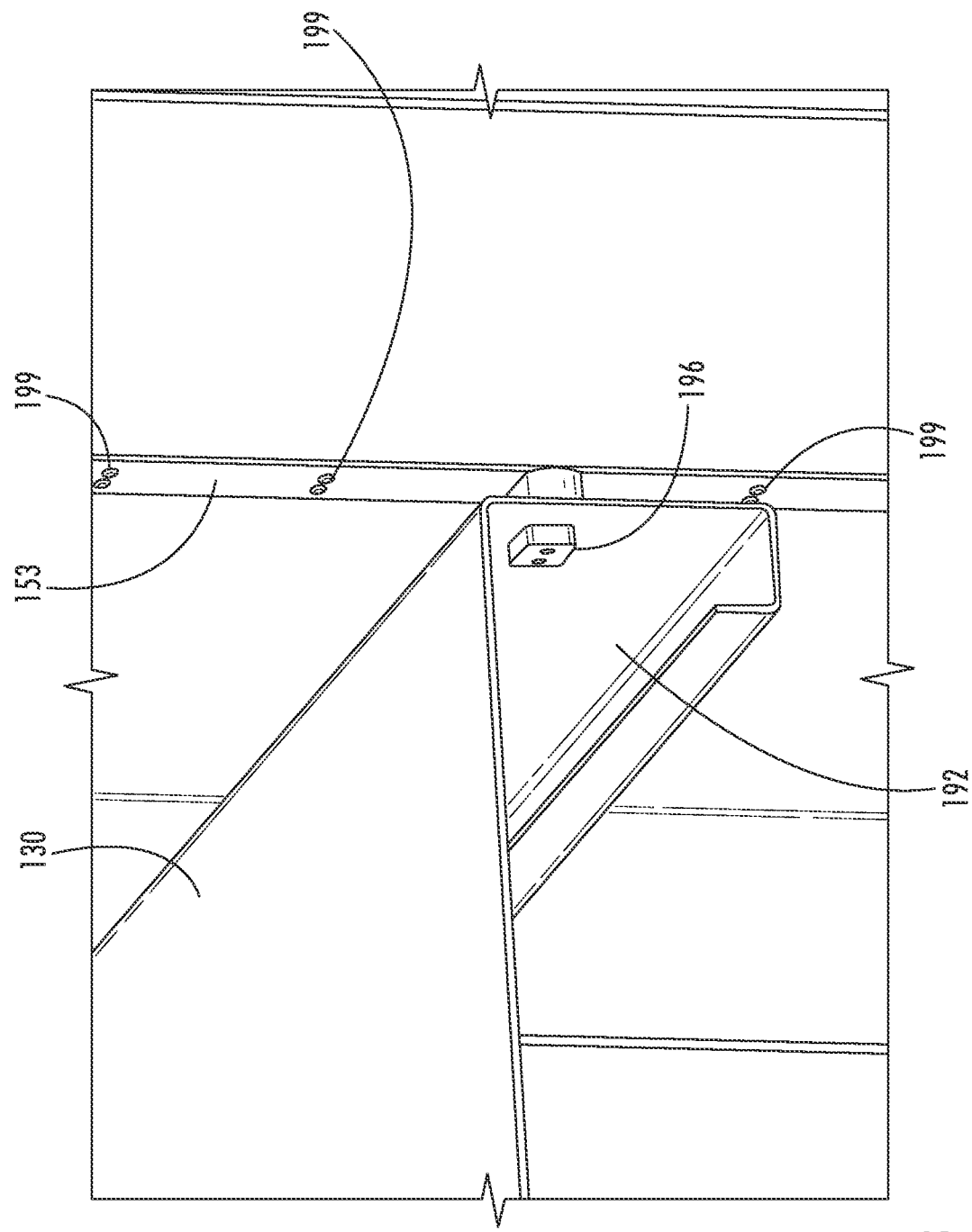
FIG. 8 is a fragmentary, perspective view of an inner side of a rear lip of a shelf of the safety cabinet of FIG. 1, illustrating a connector mounted to the shelf and a conductive strip mounted to the rear wall of the enclosure of the safety cabinet, the connector configured to be removably connected to the conductive strip at one of a plurality of indexed positions along the conductive strip to allow the shelf to be vertically adjustable while maintaining its electrical connection to a supply of electrical power.

Referring to FIG. 8, in embodiments, a rear lip 192 of each shelf 130 is equipped with a connector 196 that is electrically connected to the light source 152 mounted to the respective shelf 130. The connector 196 and the conductive strip 153 are configured to allow the connector 196 to be removably connected to the conductive strip 153 via one of a plurality of sockets 199 disposed over a range of indexed positions along the conductive strip 153 such that the light source mounted to the shelf 130 is in electrical communication with the power supply 154 via the conductive strip 153 over a range of vertical positions of the shelf 130 along the uprights 132. In embodiments, one or more of the connectors of FIGS. 15-18 can be used to help define passages through which the conductive strip extends.

Figure 15:
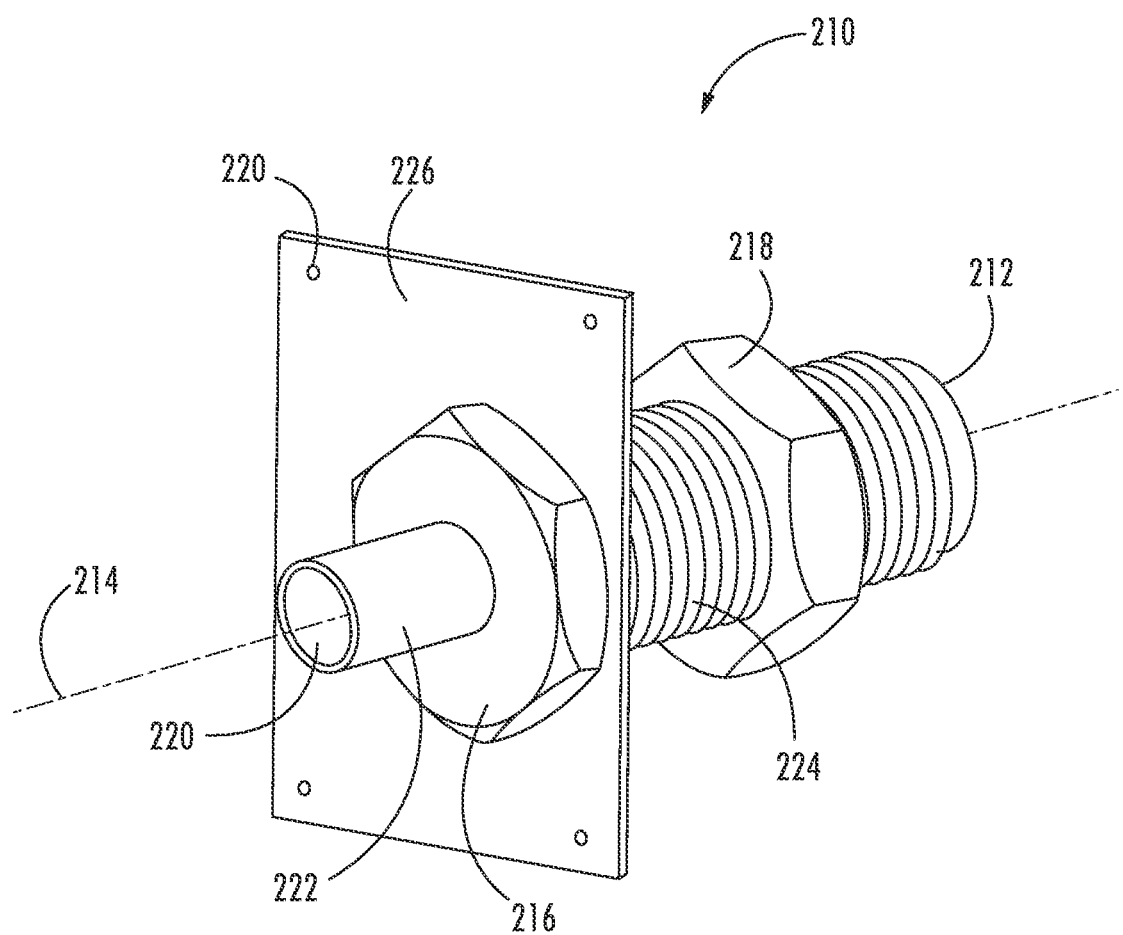
FIG. 15 is a perspective view of an embodiment of an electrical bulkhead connector that can be disposed through the enclosure of the safety cabinet to conduct electrical power to the interior lighting system.
Figure 16:
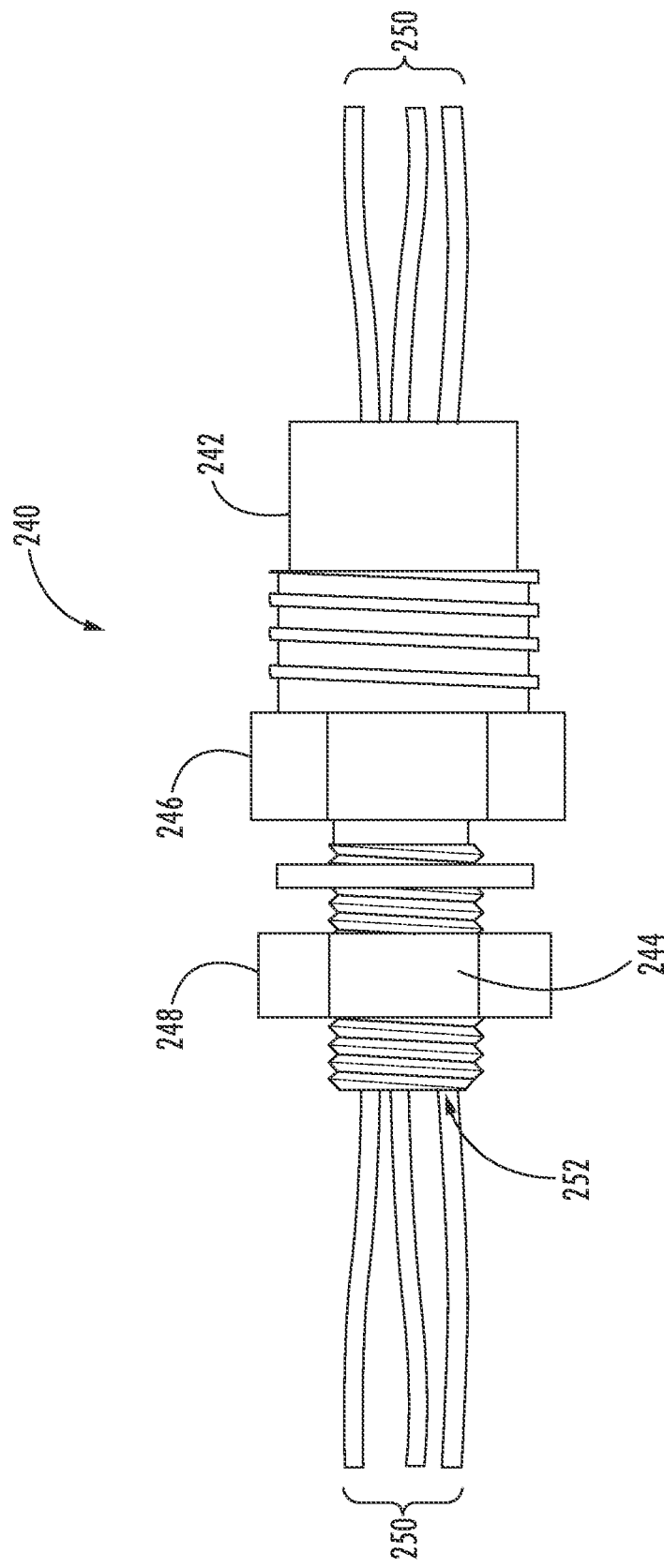
FIG. 16 is a side elevational view of an embodiment of a wire feedthrough connector that can be disposed through the enclosure of the safety cabinet to conduct electrical power to the interior lighting system.
Figure 17:
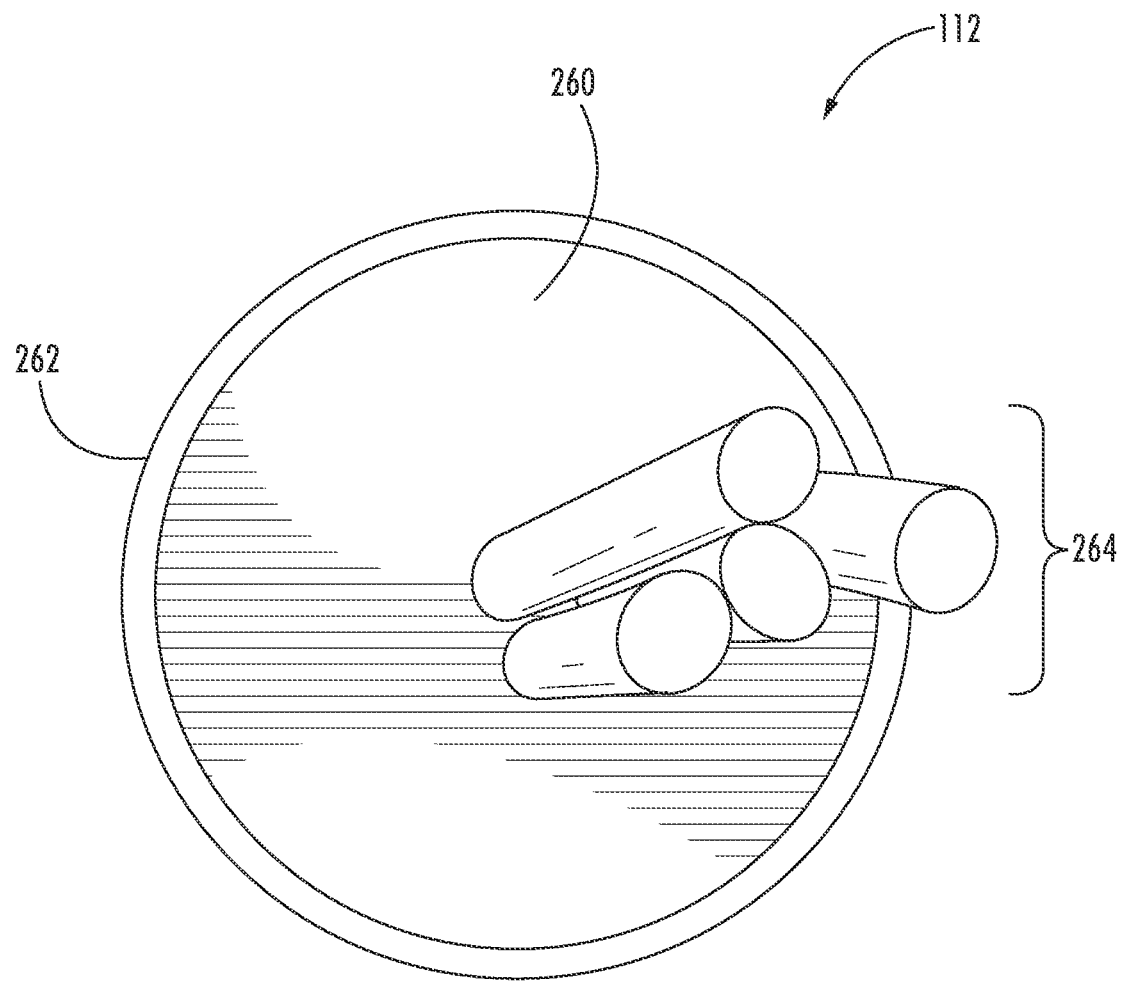
FIG. 17 is a side elevational view of an embodiment of the electrical connection that utilizes an intumescent material to seal the interior compartment of the safety cabinet.

Referring to FIGS. 1 and 6, in embodiments, the lighting system 150 can include the power supply 154 which is configured to convert standard AC supply power (110V/220V AC power) to a power suitable for use by the light sources 152 of the lighting system, such as 12V DC power for example. The power supply 154 can include a cooling fan 148 mounted externally to the enclosure 112 in a housing 149 which includes one or more connection ports for delivering supply power to an AC-DC converter 146 disposed within the top 108 of the enclosure 112 (see FIG. 6). The AC-DC converter 146 is electrically connected to the conductive strip 153 to deliver power suitable for use by the light sources 152 mounted to the shelves 130 of the safety cabinet 100. In embodiments, the power supply 154 is configured to deliver external power (110V/220V) to the internal AC-DC converter 146 to power the light sources 152 utilizing a connection system as shown in FIGS. 15-17.

Figure 9A:
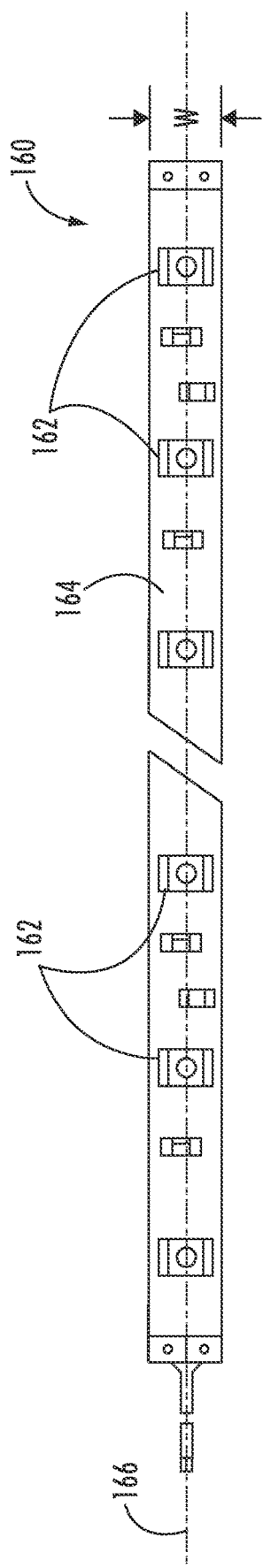
FIG. 9a is a plan view and FIG. 9b is an elevational view of an embodiment of a suitable LED ribbon strip suitable for use in embodiments of an interior lighting system constructed according to principles of the present disclosure.
Figure 9B:
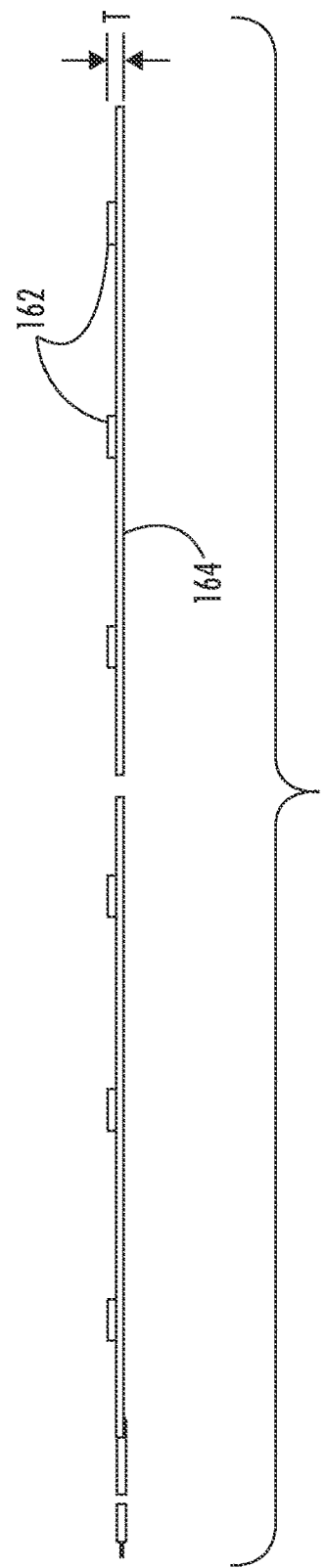

Referring to FIGS. 9a and 9b, there is an example of a light source in the form of a LED ribbon strip 160 suitable for use in an interior lighting system 150 constructed according to principles of the present disclosure that can include a plurality of LEDs 162 mounted to and spaced apart along the surface of a flat, narrow, and elongated strip or ribbon 164 that can function as a circuit board to conductively connect the LEDs. The elongated ribbon 164 may define a longitudinal axis 166 along which the plurality of LEDs 162 are disposed in axial spaced relationship to each other. The ribbon 164 can have a thickness and a width taken along a transverse cross section relative to the longitudinal axis wherein the thickness is less than the width. The ribbon 164 can be made of flexible material so that the LED ribbon strip 160 can conform to curved or uneven surfaces. Because of the low profile design of the surface mount LEDs 162 included on the ribbon 164, the LED ribbon strip 160 is relatively thin and can avoid or withstand unintended contact with foreign objects. By way of example, in embodiments, the transverse cross section of the LED ribbon strip 160 has a thickness in a range of 2-3 mm and a width in a range of 10-12 mm. In embodiments, the flexible LED ribbon strip 160 can be encased in a bezel to facilitate its mounting.

Figure 10:
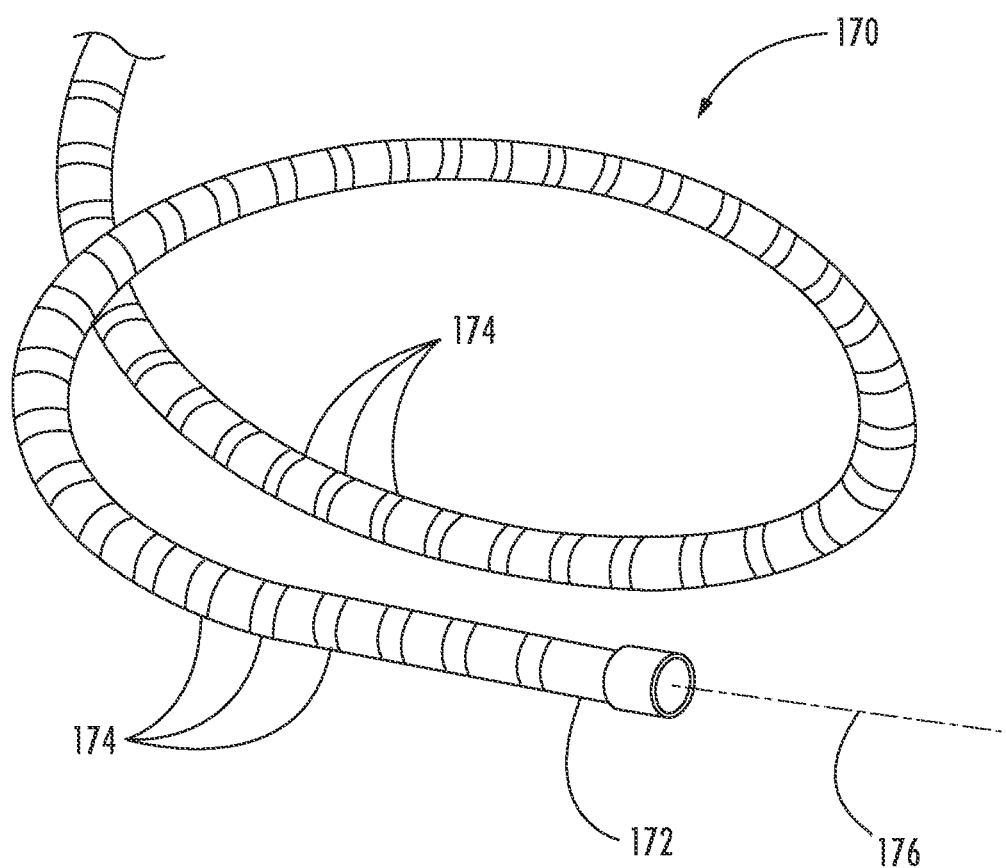
FIG. 10 is a fragmentary, perspective view of an embodiment of an LED light string suitable for use in embodiments of an interior lighting system constructed according to principles of the present disclosure.

Referring to FIG. 10, there is illustrated an example of a light source in the form of a LED light string 170 suitable for use in an interior lighting system 150 constructed according to principles of the present disclosure in which the light source comprises a plurality of LEDs 172 that are disposed within and encased by an elongated string 174. The elongated string 174 can be made of a transparent material such as rubber or plastic so that light emitted from the LEDs 172 projects from the LED light string 170. The elongated string 174 may define a longitudinal axis 176 along which the plurality of LEDs 172 is axially spaced apart. The elongated string 174 may also be flexible to conform to different mounting arrangements and may have a circular cross-section and a consistent diameter over its length. In a further embodiment, the interior light system may include LEDs operatively associated with one or more flexible, fiber optic waveguides to facilitate conduction of light through the interior compartment of the safety cabinet. The fiber optic waveguide can include a transparent core made from drawn glass or silica for the conduction of light and a cladding layer coated about the core to internally reflect and direct some light through the waveguide while allowing some light to transmit from the waveguide, thereby illuminating the interior compartment. In other embodiments, the LEDs or another type of light source may be operatively associated with a rigid light bar.

Figure 11:
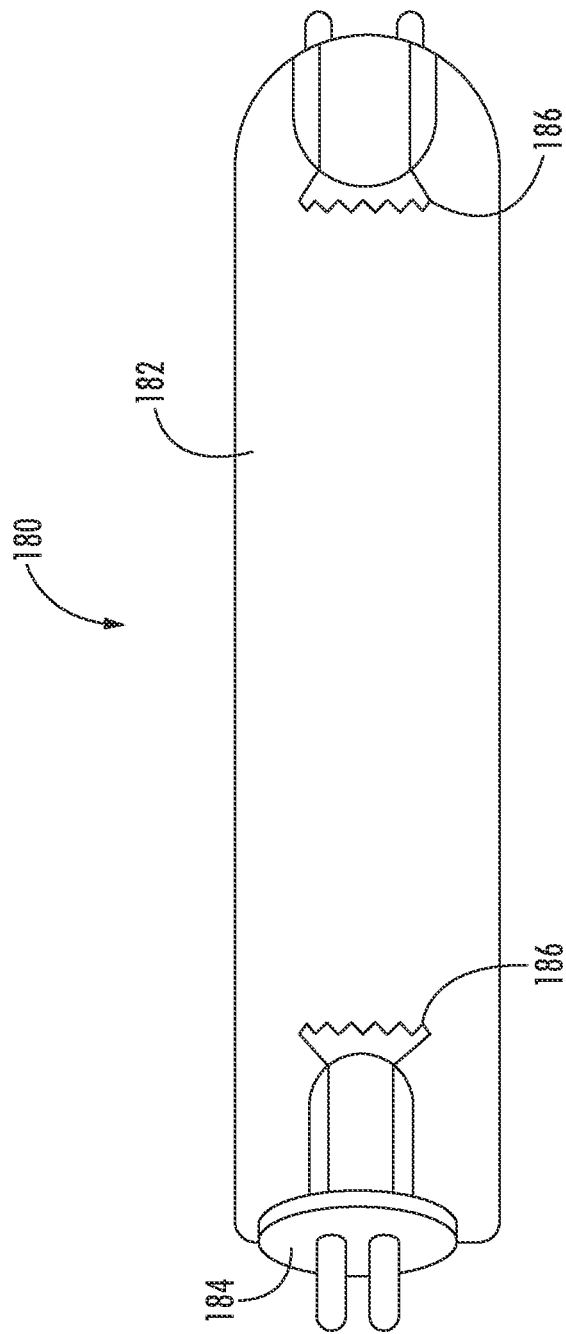
FIG. 11 is a perspective view of an embodiment of an ultraviolet lamp suitable for use in embodiments of an interior lighting system constructed according to principles of the present disclosure.

Referring to FIG. 11, there is illustrated another embodiment of a light source suitable for use in an interior lighting system 150 constructed according to principles of the present disclosure in which the light source comprises an ultraviolet ("UV") lamp 180. The ultraviolet lamp 180 can emit wavelengths in the ultraviolet range. In embodiments, the UV lamp 180 can comprise any suitable device configured to emit UV light, such as a commercially-available UV-C (germicidal) lamp, for example.

In an embodiment, the ultraviolet lamp 180 can include an elongated hollow tube 182 made of a transparent material such as glass that contains an inert gas or a noble gas such as, for example, mercury or argon. The interior of the hollow tube 182 may be coated with an iridescent material such as phosphor, although in other embodiments the coating may be omitted. Located at either end or base 184 of the tube 182 can be an electrode 186, which may specifically be a hot cathode arranged to direct a stream of electrons across the axial length of the tube when conductively coupled to a power source. When electrons are directed through the gas between the two electrodes disposed in the tube 182, interaction between the electrons and the gas atoms causes the gas atoms to become ionized and emit photons, which may be in the ultraviolet frequency range. In another embodiment, the ultraviolet lamp can be a LED light made from an appropriate semiconductor material.

In embodiments, ultraviolet lamps can be provided in the interior lighting system 150 so that the ultraviolet light or radiation is capable of killing microorganisms like bacteria, viruses, and other pathogens through irradiation. The ultraviolet light can therefore sterilize and disinfect the interior compartment 114 of the safety cabinet 100. This is advantageous when the contents of the safety cabinet 100 are susceptible to contamination from microorganisms or pathogens. To promote effective irradiation with ultraviolet light, the light sources of the interior lighting system should be configured so that ultraviolet lamps are located to provide maximum exposure to the interior compartment and the contents of the safety cabinet. In embodiments of an interior lighting system constructed in accordance with principles of the present disclosure including a light source in the form of a UV lamp, the lighting system can include a safety switch configured to interrupt the power supply to the UV lamp unless each door of the safety cabinet is in the closed position. If a door of the safety cabinet is moved to an open position, the safety switch can be configured to deactivate each UV lamp so that the emission of UV light is disrupted when a door of the safety cabinet is opened to protect people from UV exposure. In embodiments, the safety switch can comprise one or more Hall Effect sensors configured to detect the doors of the safety cabinet in the closed position.

Figure 12:
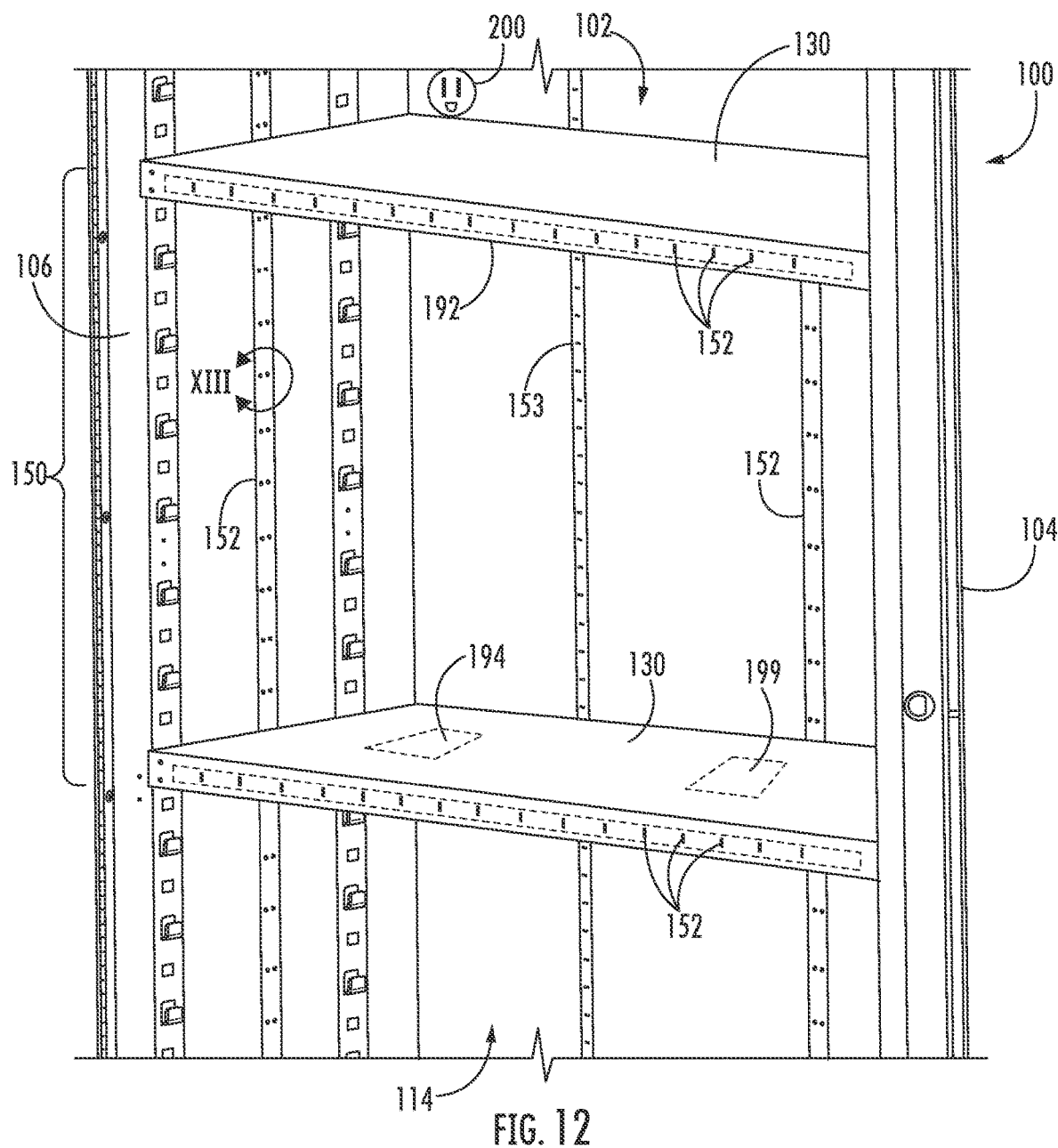
FIG. 12 is a perspective view of the interior compartment of the safety cabinet showing possible locations for mounting the light sources of the interior lighting system in accordance with aspects of the disclosure.

Referring to FIG. 12, the interior light system 150 can be mounted or supported in the interior compartment 114 at a location where it can sufficiently illuminate the contents of the safety cabinet 100. In an embodiment, the plurality of light sources 152 included with the interior lighting system 150 can be attached along the interior surface 116 of the enclosure 112 such as, for example, along the interior surface 116 of the rear wall 102. In embodiments, one or more light sources 152, such as LED ribbon strips or LED light strings, can extend behind the shelves 130, which may be offset from the rear wall 102, so that the emitted light is directed forwardly to illuminate items that may be set on the shelves 130. In embodiments, any suitable technique can be used to secure the light source 152 to at least one of the shelf 130 and the enclosure 112. For example, in embodiments, adhesive, magnets, and/or sheet metal fasteners can be used to secure the light source 152 (e.g., LED ribbon strips or LED light strings) to the interior surface 116 of the enclosure 112 and/or the one of the shelves 130.

In a further embodiment, one or more light sources 152, such as the LED ribbon strips and/or LED light strings, for example, may be attached to the interior surfaces of the first and second sidewalls 104, 106 in addition to or instead of the rear wall 102. The light source(s) 152 can extend from generally proximate the top 108 to the bottom 110 to illuminate the vertical extension of the interior compartment 114. In an embodiment, the interior lighting system 150 may include multiple LED strips or strings that are spaced apart from each other to illuminate the interior compartment 114 from multiple angles.

Figure 13:
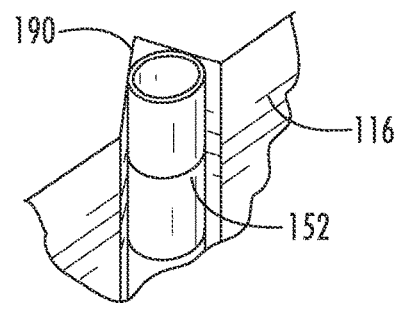
FIG. 13 is an enlarged, detail view of the area indicated by arrow 13-13 of FIG. 12, illustrating a part of the interior lighting system accommodated in a channel notch disposed into an interior surface of the safety cabinet.

Referring to FIG. 13, in an embodiment, to accommodate the electrical lamps of the interior lighting system 150 in a manner that will not interfere with the shelves 130, one or more grooves or channel notches 190 can be disposed in the interior surface 116 of the enclosure 112. For example, the channel notches 190 can extend in the vertical direction and can be formed in one or more of the rear wall or the first and second sidewalls by a bending process during construction of the safety cabinet 100. The channel notches 190 may have a V-shape, a U-shape, or another suitable shape. The interior lighting system 150, which may be a LED ribbon strip or a LED light string, or may be an ultraviolet lamp, can be set into the channel notches 190 so that it is practically removed from the majority of the interior compartment 114 and will not interfere with the shelves 130 that can abut the interior surface 116 of the enclosure 112.

Referring to FIG. 12, in another embodiment, the interior lighting system 150 can be located on one or more of the shelves 130 disposed in the interior compartment 114 of the safety cabinet 100. For example, the interior lighting system 150 which may be LED ribbon strips or LED light strings, or may be ultraviolet lamps, can be attached to the inner surface of the front lip 191 of each shelf 130 or can be attached to the forward edge 192 of each shelf 130. In addition, light sources associated with the interior lighting system 150 can be located on the underside of the top 108. In an embodiment, the light sources of the interior lighting system 150 can be incorporated into the structure of the shelves 130, for example, into cavities 194 (indicated in dashed lines) disposed into the underside of the shelf 130 or into channels notches 190 disposed along the forward edge 192 of the shelf. Accordingly, the shelves 130 and the light sources 152 of the interior lighting system 150 can be preassembled prior to inclusion in the safety cabinet 100 and further can be sold separately for customization of the safety cabinet.

In embodiments, the interior lighting system 150 can be operatively associated with power switches for turning on or off the plurality of electrical lamps. For example, the switch may be operatively triggered by the first and/or second doors 124, 126 so that the interior lighting system 150 turns on when the doors are opened and turns off when the doors are closed. In embodiments where the light sources comprise UV lamps, the switch can be configured to turn the interior lighting system on when the doors are closed to disinfect the interior compartment and contents of the safety cabinet and to turn the UV lamps off when a door of the safety cabinet is opened to protect those located near the safety cabinet from exposure to the UV light.

Figure 14:
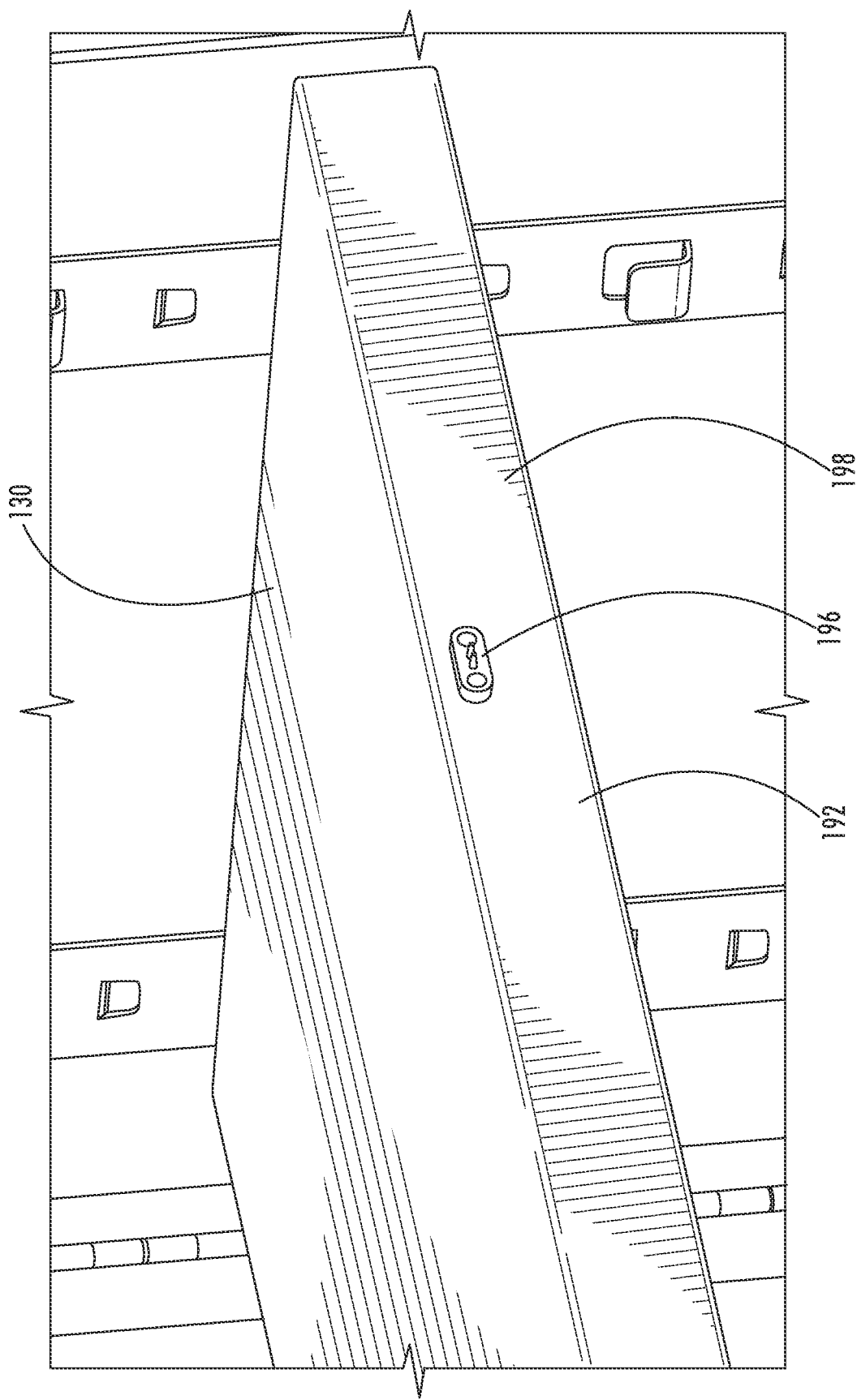
FIG. 14 is a rear perspective view of an embodiment of a shelf that may be disposed in the safety cabinet that includes an electrical connector to provide power to light sources that may be operatively associated with the shelf.

Referring to FIG. 14, in the embodiments in which the light sources of the interior lighting system 150 are incorporated into the structure of the shelves 130, each shelf 130 can include the electrical connector 196 projecting from an outer surface 198 of the rear lip 192 of the shelf 130. In the illustrated embodiment, the electrical connector 196 can mate with a corresponding two-pronged socket 199. The electrical connector 196 can be mounted to the surface of the shelf 130 and can mate with one of a plurality of mating sockets 199 disposed along the length of the conductive strip 153 (see also, FIG. 8) to receive electricity from the power supply 154. The electrical connector 196 can be connected via wires or conductors that extend through the channel defined by the lips of the shelf 130 to the light source(s) 152 mounted to the respective shelf 130 to conduct electricity to the light source(s) 152. Inclusion of the electrical connector 196 further facilitates the preassembly of the shelves 130 and the possible customization of safety cabinets through aftermarket sales of the shelves 130.

In other embodiments, other components in addition to, or in substitution for, the electrical connector 196 and the socket 199 can be used to provide the mating electrical interconnection between the light source 152 of the shelf 130 and the power supply. For example, in other embodiments, a two-part, twist-lock style electrical connector can be used in place of the electrical connector 196 and the socket 199. In embodiments, one part of the twist-lock electrical connector is configured to be inserted into the other part and rotated relative to the other part (e.g., ninety degrees) to lock the two parts together and to form an electrical path between the light source 152 of the shelf 130 and the power supply.

Figure 2:
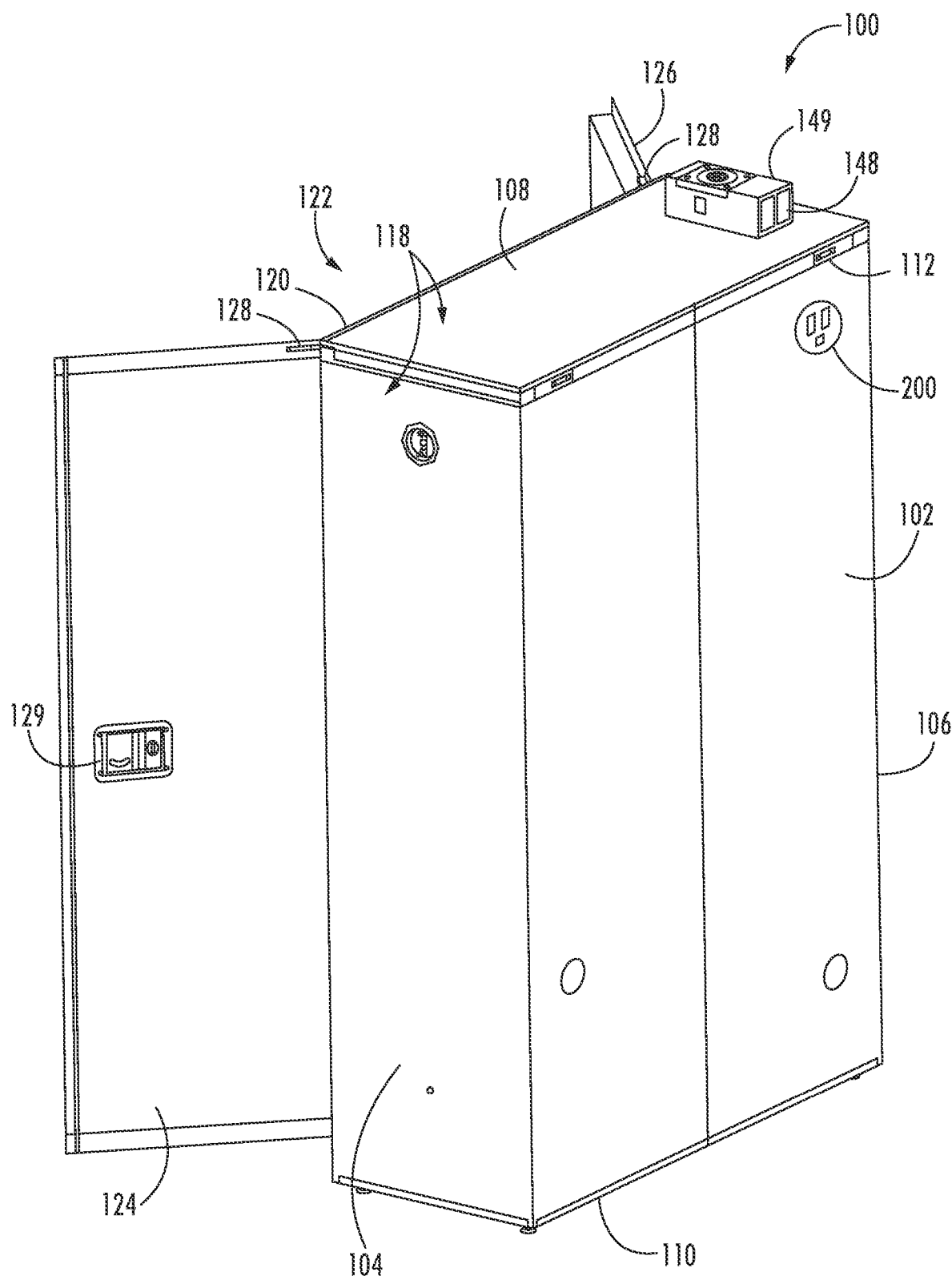
FIG. 2 is a rear perspective view of the safety cabinet of FIG. 1, illustrating one of a variety of possible locations for an electrical power supply of the interior lighting system through the enclosure to conduct electrical power to the interior lighting system in the interior compartment.
Figure 3:
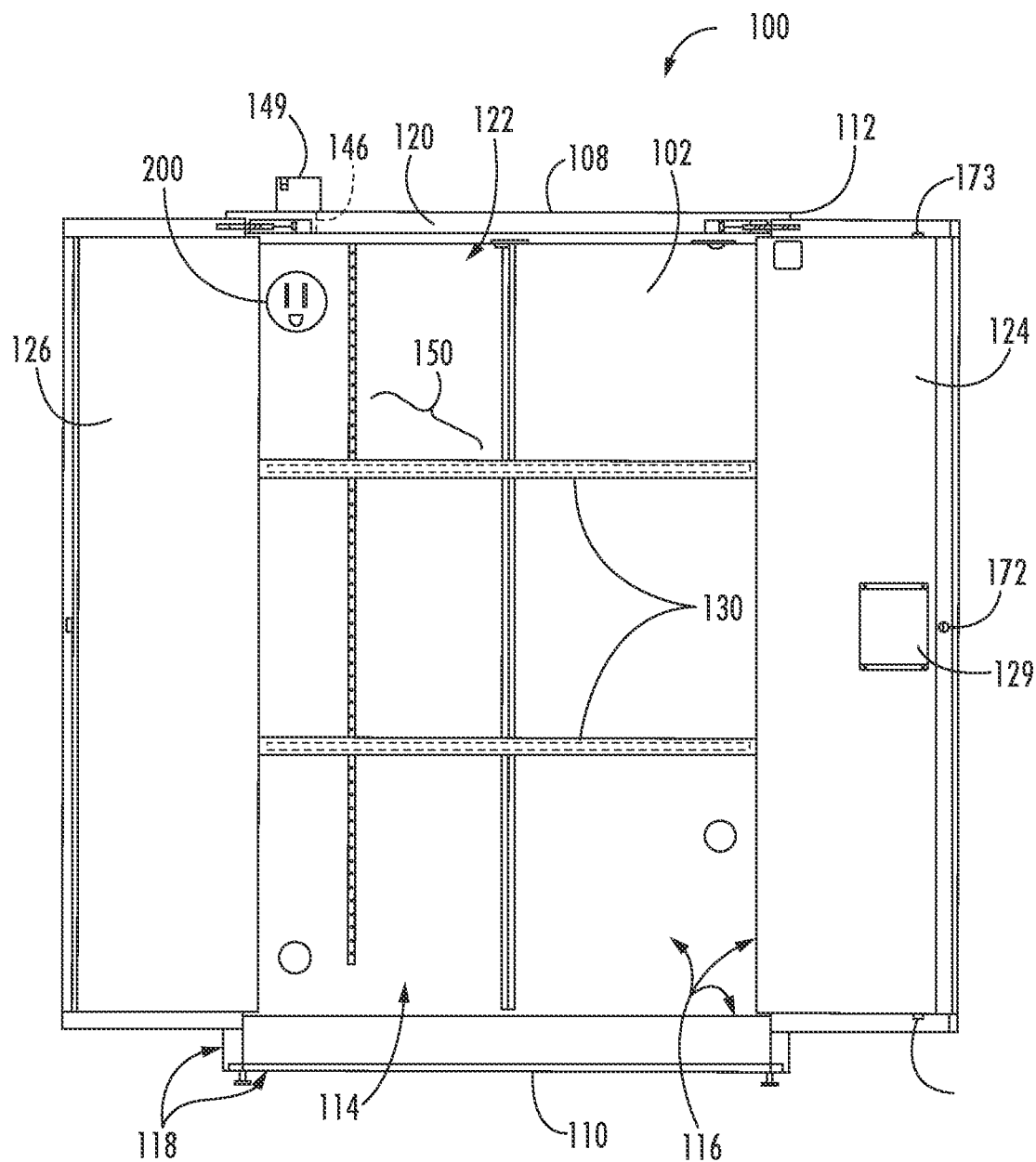
FIG. 3 is a front elevational view of the safety cabinet of FIG. 1, illustrating a pair of doors in an open position and a plurality of horizontally arranged shelves disposed in the interior compartment defined by the enclosure.
Figure 4:
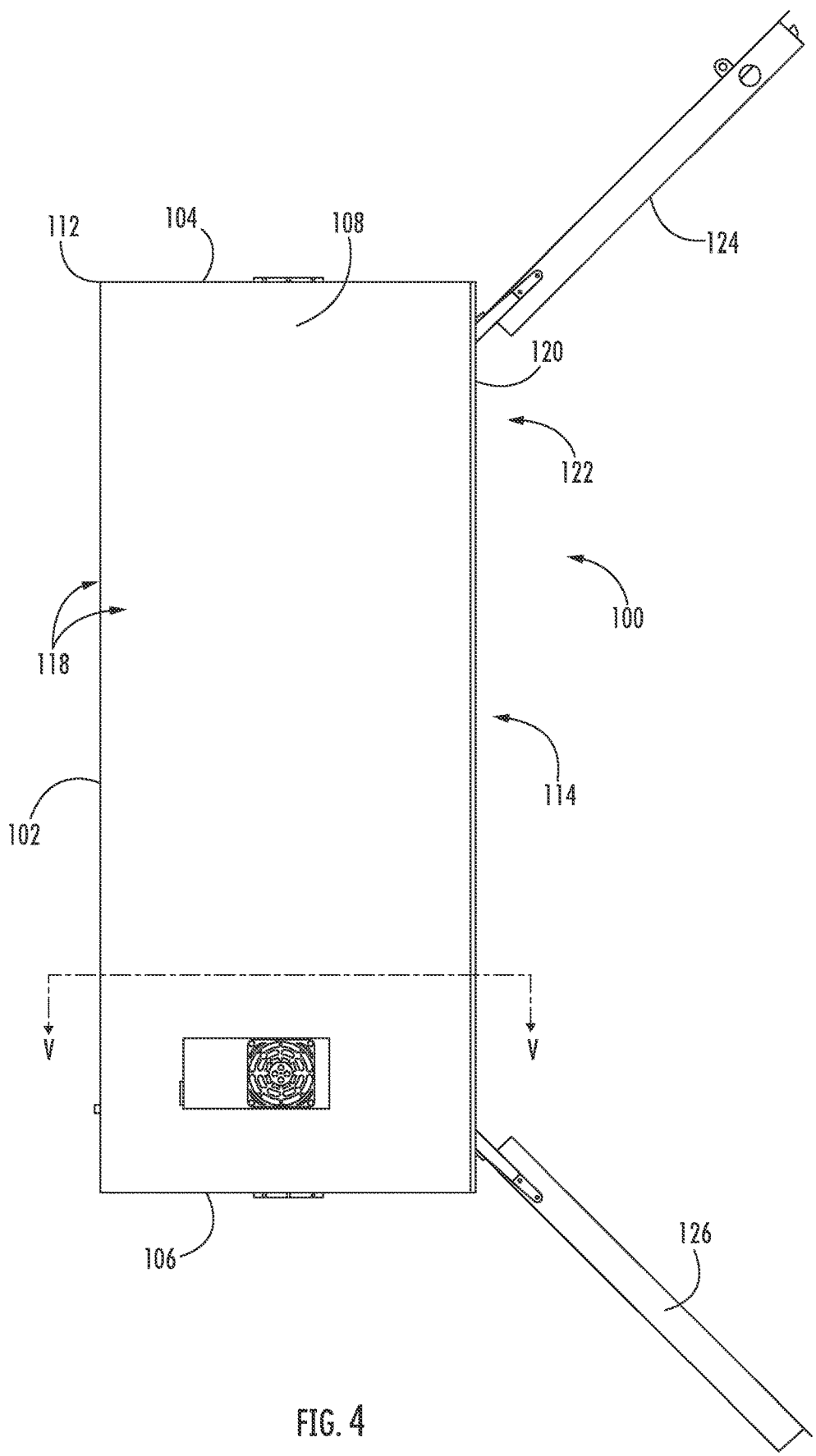
FIG. 4 is a top plan view of the safety cabinet of FIG. 1, illustrating the electrical power supply of the interior lighting system.

To provide power to operate the interior lighting system 150 while maintaining the structural integrity of the safety cabinet 100, an electrical connection 200 can be established through the enclosure 112 to provide electrical communication with the interior compartment 114 from the power source 154, or other suitable power source such as a wall outlet coupled to the electrical grid or other power source, such as batteries, for example, to the conductive strip 153. Referring to FIGS. 2, 3, and 12, the electric connection 200 (represented schematically) can be positioned at a suitable location on the enclosure 112 to protect and preserve the integrity of the electrical connection. For example, the electrical connection 200 can be disposed through the rear panel 102 and can be located at a vertically elevated position proximate the top 108 so that the electrical connection is removed from contamination or spillage that may gather on the bottom 110 of the enclosure 112. Other relatively protected locations for the electrical connection 130 include the top 108 and the upper areas of the first and/or second sidewall 104, 106, although the disclosure contemplates any possible location on the enclosure for the electrical connection 130. To preserve compliance with any safety ratings assigned to the safety cabinet such as FM Approvals, the electrical connection 200 can be designed to isolate the interior compartment 114 from the surrounding environment. Examples of suitable electrical connections include but are not limited to electrical bulkhead connectors, wire feedthrough connectors, and/or connections potted or sealed in an intumescent material.

Referring to FIG. 15, there is illustrated an embodiment of an electrical bulkhead connector 210 that can be used to direct electricity into the enclosure of the safety cabinet, however, it should be noted that bulkhead connectors are available in various different designs and FIG. 15 is only an example. Bulkhead connectors 210 are designed to be inserted through a hole or cutout formed in a panel or wall of the equipment of interest. The bulkhead connector 210 has an elongated body 212 that may extend along a connector axis 214 and that can be mounted through the wall to which the connector is installed. To mount the bulkhead connector 210, the elongated body 212 of the bulkhead connector can include a fixed flange nut or fixed backing nut 216 and an associated movable securing nut 218 which can be tightened to clamp the enclosure wall between the backing nut and securing nut. In embodiments, the connector 210 may be used for power and/or data/sensor signal transmission. The bulkhead connector is also chosen to not melt in a fire which would expose the interior (potentially flammable contents) to an external fire and create a more dangerous situation.

The elongated body 212 of the bulkhead connector 210 can be wholly or partly made of a non-conductive material in which one or more conductive terminals or conductive contacts 220 are disposed. The conductive contact 220 can substantially extend across the axial length of the elongated body 212 and can be supported in an insulative support 222 made of the non-conductive material to prevent electrical shorting. In some embodiments, the electrical bulkhead connector 210 may have a single conductive contact 220 or pin constructed, for example, in a coaxial arrangement and in other embodiments may have a plurality of conductive contacts. The elongated body 212 may have external features such as external threads 224 or a bayonet mount that enables the electrical bulkhead connector to connect with the power source. The external threads 224 can facilitate tightening of the securing nut 218 to the backing nut 216.

In an embodiment, to close the cutout formed into the wall in which the bulkhead connector 210 is installed, a flange cover 226 may be associated with the bulkhead connector. The flange cover 226 may be a flat, planar plate made of a non-flammable material such as metal. The flange cover 226 can have any suitable shape such as rectangular, square, or circular. In an embodiment, the flange cover 226 can be joined to or abutted against the fixed backing nut 216 and oriented toward the securing nut 218. When the bulkhead connector 210 is installed in the cutout, the cover flange 226 can be placed flush against the interior or exterior surface of the wall of the enclosure to minimize airflow through the cutout and generally isolate the interior compartment. In an embodiment, the flange cover 226 can include one or more apertures 228 that can accommodate fasteners such as sheet metal screws or rivets to secure the flange cover to the wall of the enclosure.

Referring to FIG. 16, there is illustrated an embodiment of a wire feedthrough connector 240 that can be used as the electrical connection mounted through the enclosure. The wire feedthrough connector 240 is similar to the electrical bulkhead connector and includes an elongated body 242 defining a connector axis 244 and that is configured to mount to and pass through a hole or cutout formed in a wall. To mount to the wall, the wire feedthrough connector may include a fixed backing nut 226 and a movable securing nut 228 that can be moved together to clamp the wall. Wire feedthrough connectors 240 differ in that they are configured to receive conductive wires 250 that are passed through a bore or lumen 252 disposed through the elongated body 242. Disposed in the elongated body 242 may be elastomeric material such as a rubber donut or ring that can grip around and secure the wires. The wire feedthrough connector 240 is therefore a more permanent design of an electrical connector. The wire feedthrough connector may also be operatively associated with a flange cover to cover the cutout as described above.

Referring to FIG. 17, in an embodiment, the electrical connection 200 can include an intumescent compound or material. Intumescent compounds are capable of swelling or expanding when subjected to heat or fire. Accordingly, when exposed to heat or fire, the intumescent compound can expand around the conductive contacts or wires in the electrical connector to ensure the interior compartment of the safety cabinet is isolated. Examples of intumescent materials include carbonates, graphite, silicates, and ceramics. In the illustrated embodiment, to accommodate the intumescent material 260, a cutout can be formed in the wall of the enclosure 112 and a tubular, hollow, sleeve 262 of cardboard, plastic, or sheet metal can be inserted through the cutout. The intumescent material 260, which may be in the form of a putty or paste, can be pressed into the sleeve 262 and a plurality of conductive wires 264 can be pushed or directed through the intumescent material. The intumescent material 260 can therefore function as a sealing or potting material to secure the conductive wires 264 in place while isolating the interior compartment of the safety cabinet. In possible embodiments, the intumescent material can be used as the insulative material that supports the conductive contact in the bulkhead connector and/or wire feedthrough connector described above.

Embodiments of a safety cabinet having an interior lighting system with at least one UV light source constructed according to principles of the present disclosure can be used to carry out a method of disinfecting an interior compartment. In embodiments, a method of disinfecting an interior compartment following principles of the present disclosure can be used with any embodiment of a safety cabinet having a suitable interior lighting system configured to provide disinfecting functionality according to principles discussed herein.

In one embodiment, a method of disinfecting an interior compartment of a safety cabinet can be used in which the safety cabinet includes an enclosure and at least one door. The enclosure includes an inner shell and an outer shell in a double walled configuration. The inner shell defines an interior compartment and a compartment opening. The interior compartment is accessible via the compartment opening, and the at least one door is rotatably mounted to the enclosure and moveable over a range of travel between an open position and a closed position. The at least one door is adapted to occlude the compartment opening of the enclosure when the at least one door is in the closed position.

The method includes electrically connecting an interior lighting system disposed in the interior compartment to an external electrical component via an electrical connection disposed through the inner shell and the outer shell of the enclosure and configured to isolate the interior compartment from an exterior environment. The compartment opening is occluded by moving each of the at least one door to the closed position. At least one ultraviolet light source of the interior lighting system is activated for a predetermined period of time sufficient to reduce at least one of a microorganism and a pathogen disposed within the interior compartment.

In embodiments, methods of disinfecting include interrupting a supply of power to the interior lighting system when the at least one door is moved from the closed position to an open position. In at least some of such embodiments, the supply of power can be restored to the interior lighting system when the at least one door is moved back to the closed position.

In embodiments, methods of disinfecting include storing an item in the interior compartment of the safety cabinet. The at least one ultraviolet light source can be activated after the item is stored in the interior compartment.

In embodiments, methods of disinfecting include attaching the at least one ultraviolet light source to a shelf adjustably mounted to the enclosure within the interior compartment in one of a range of indexed vertical positions. The at least one ultraviolet light source can be removably connected to the external electrical component via an electrical connector mounted to the shelf and electrically connected to the at least one light source and a conductive strip mounted to the enclosure. The conductive strip can be disposed along a vertical axis and include a plurality of sockets disposed over the range of indexed vertical positions. The electrical connector can be configured to be removably connected to the conductive strip via a respective one of a plurality of sockets of the conductive strip.

The disclosure has described various embodiments of a safety cabinet with an interior lighting system. Such examples are non-limiting, and do not define or limit the scope of the disclosure in any way. By way of example, further or particular embodiments in accordance with the disclosure include:

Embodiment 1. A safety cabinet comprising:
an enclosure defining an interior compartment that is accessible through a compartment opening defined by the enclosure;
a door being rotatably mounted to the enclosure and moveable over a range of travel between an open position and a closed position, the door adapted to cover at least a portion of the opening of the enclosure when the door is in the closed position;
an interior lighting system including at least one light source disposed in the interior compartment; and
an electrical connection disposed through the enclosure and conductively connected to the interior lighting system, the electrical connection configured to isolate the interior compartment from an exterior environment.

Embodiment 2. The safety cabinet of embodiment 1, wherein the at least one light source of the interior lighting system comprises a light emitting diode ("LED").

Embodiment 3. The safety cabinet of embodiment 1, wherein the at least one light source of the interior lighting system comprises a plurality of LEDs arranged as an LED ribbon strip.

Embodiment 4. The safety cabinet of embodiment 3, wherein the LED ribbon strip has a thickness in a range between 2 mm and 4 mm and a width in a range between 8 mm and 14 mm.

Embodiment 5. The safety cabinet of embodiment 1, wherein the at least one light source of the interior lighting system comprises a plurality of LEDs arranged as an LED light string.

Embodiment 6. The safety cabinet of embodiment 1, wherein the at least one electric lamp of the interior lighting system comprises an ultraviolet ("UV") lamp adapted to emit UV light for disinfecting the interior compartment.

Embodiment 7. The safety cabinet of embodiment 6, wherein the ultraviolet lamp is a fluorescent lamp with a transparent tube containing a conductive gas.

Embodiment 8. The safety cabinet of embodiment 1, wherein the interior lighting systems includes a fiber optic waveguide.

Embodiment 9. The safety cabinet of embodiment 1, wherein the at least one electric lamp of the interior lighting system is attached to an interior surface of the enclosure.

Embodiment 10. The safety cabinet of embodiment 9, wherein the interior surface defines a channel notch disposed therein for accommodating the electric lamp of the interior lighting system.

Embodiment 11. The safety cabinet of embodiment 10, where the channel notch is one of V-shaped and U-shaped.

Embodiment 12. The safety cabinet of embodiment 11, wherein the channel notch extends between proximate a top of the enclosure to proximate a bottom of the enclosure.

Embodiment 13. The safety cabinet of embodiment 1, further comprising a shelf disposed in the interior compartment.

Embodiment 14. The safety cabinet of embodiment 13, wherein the at least one electric lamp is attached the shelf.

Embodiment 15. The safety cabinet of embodiment 14, wherein the at least one electric lamp is located on an underside of the shelf.

Embodiment 16. The safety cabinet of embodiment 14, wherein the at least one electric lamp is located on a forward edge of the shelf.

Embodiment 17. The safety cabinet of embodiment 14, wherein the at least one electric lamp is incorporated in the shelf and the shelf includes an electrical connector conductively connected to the at least one electric lamp.

Embodiment 18. The safety cabinet of embodiment 1, wherein the electrical connection includes a bulkhead connector disposed through a cutout formed in the enclosure.

Embodiment 19. The safety cabinet of embodiment 18, wherein the bulkhead connector includes a conductive contact supported in an insulative support.

Embodiment 20. The safety cabinet of embodiment 19, wherein the bulkhead connector includes an elongated body having an external thread and a securing nut that can be threadedly moved with respect to a backing nut fixed to the elongated body.

Embodiment 21. The safety cabinet of embodiment 18, wherein the bulkhead connector includes a flange cover adapted to cover the cutout formed in the enclosure.

Embodiment 22. The safety cabinet of embodiment 1, wherein the electrical connection is wire feedthrough connector including an elongated body defining a lumen to accommodate a conductive wire passing through the enclosure.

Embodiment 23. The safety cabinet of embodiment 1, wherein the electrical connection includes a conductive cable disposed through a cutout formed in the enclosure.

Embodiment 24. The safety cabinet of embodiment 23, wherein the electrical connection includes an intumescent material sealing or potting the conductive cable in the cutout.

Embodiment 25. The safety cabinet of embodiment 24, wherein the intumescent material comprises at least one of a carbonate, a graphite, a silicate, and a ceramic.

Embodiment 26. The safety cabinet of embodiment 1, wherein the enclosure is of a double panel construction including an external panel and an internal panel defining an air gap there between.

Embodiment 27. The safety cabinet of embodiment 26, wherein the enclosure further includes insulation disposed between the external panel and the internal panel.

Embodiment 28. The safety cabinet of embodiment 1, wherein the safety cabinet is FM approved.

Embodiment 29. A method of disinfecting contents in a safety cabinet comprising:

storing a plurality of contents in an interior compartment of an enclosure;

closing a compartment opening defined by the enclosure for accessing the interior compartment; and activating, for a predetermined period of time, an interior lighting system including an ultraviolet lamp disposed in the interior compartment.

Embodiment 30. The method of embodiment 29, wherein the interior lighting system receives electrical power via an electrical connection disposed through the enclosure and configured to isolate the interior compartment from an exterior environment.

All references, including publications, patent applications, and patents, cited herein are hereby incorporated by reference to the same extent as if each reference were individually and specifically indicated to be incorporated by reference and were set forth in its entirety herein.

The use of the terms "a" and "an" and "the" and similar referents in the context of describing the invention (especially in the context of the following claims) are to be construed to cover both the singular and the plural, unless otherwise indicated herein or clearly contradicted by context. The terms "comprising," "having," "including," and "containing" are to be construed as open-ended terms (i.e., meaning "including, but not limited to,") unless otherwise noted. Recitation of ranges of values herein are merely intended to serve as a shorthand method of referring individually to each separate value falling within the range, unless otherwise indicated herein, and each separate value is incorporated into the specification as if it were individually recited herein. All methods described herein can be performed in any suitable order unless otherwise indicated herein or otherwise clearly contradicted by context. The use of any and all examples, or exemplary language (e.g., "such as") provided herein, is intended merely to better illuminate the invention and does not pose a limitation on the scope of the invention unless otherwise claimed. No language in the specification should be construed as indicating any non-claimed element as essential to the practice of the invention.

Preferred embodiments of this invention are described herein, including the best mode known to the inventors for carrying out the invention. Variations of those preferred embodiments may become apparent to those of ordinary skill in the art upon reading the foregoing description. The inventors expect skilled artisans to employ such variations as appropriate, and the inventors intend for the invention to be practiced otherwise than as specifically described herein. Accordingly, this invention includes all modifications and equivalents of the subject matter recited in the claims appended hereto as permitted by applicable law. Moreover, any combination of the above-described elements in all possible variations thereof is encompassed by the invention unless otherwise indicated herein or otherwise clearly contradicted by context.

What is claimed is:

1. A safety cabinet comprising:
   an enclosure defining an interior compartment and a compartment opening, the interior compartment being accessible via the compartment opening;
   a door being rotatably mounted to the enclosure and moveable over a range of travel between an open position and a closed position, the door adapted to cover at least a portion of the compartment opening of the enclosure when the door is in the closed position;
   an interior lighting system including at least one light source disposed in the interior compartment; and an electrical connection conductively connected to the interior lighting system, the electrical connection arranged with the enclosure and configured to be electrically connected to an external electrical component such that the interior compartment is isolated from an exterior environment via the electrical connection;

wherein the at least one light source of the interior lighting system is attached to an interior surface of the enclosure, and the interior surface defines a channel configured to accommodate therein the at least one light source of the interior lighting system.

2. The safety cabinet of claim 1, wherein the at least one light source of the interior lighting system comprises a light emitting diode ("LED").

3. The safety cabinet of claim 1, wherein the at least one light source of the interior lighting system comprises a plurality of LEDs arranged as an LED light string.

4. The safety cabinet of claim 1, wherein the at least one light source of the interior lighting system comprises a plurality of LEDs arranged as an LED ribbon strip, the LED ribbon strip defining a longitudinal axis along which the plurality of LEDs are disposed in axial spaced relationship to each other, and the LED ribbon strip having a thickness and a width taken along a transverse cross section relative to the longitudinal axis wherein the thickness is less than the width.

5. The safety cabinet of claim 4, wherein the thickness of the LED ribbon strip is in a range between 2 mm and 4 mm, and the width of the LED ribbon strip is in a range between 8 mm and 14 mm.

6. The safety cabinet of claim 1, wherein the at least one light source of the interior lighting system comprises an ultraviolet ("UV") light source adapted to emit UV light.

7. The safety cabinet of claim 6, wherein the interior lighting system includes a safety switch configured to interrupt the power supply to the UV light source when the door is not in the closed position.

8. The safety cabinet of claim 1, wherein the electrical connection comprises a wire feedthrough connector including an elongated body defining a lumen to accommodate a conductive wire passing through the enclosure.

9. The safety cabinet of claim 1, wherein the electrical connection includes a conductive cable disposed through a cutout formed in the enclosure.

10. The safety cabinet of claim 9, wherein the electrical connection includes an intumescent material sealing or potting the conductive cable in the cutout.

11. The safety cabinet of claim 1, wherein the electrical connection includes a bulkhead connector disposed through a cutout defined in the enclosure.

12. The safety cabinet of claim 11, wherein the bulkhead connector includes a flange cover adapted to cover the cutout formed in the enclosure.

13. The safety cabinet of claim 11, wherein the bulkhead connector includes a conductive contact supported in an insulative support.

14. The safety cabinet of claim 13, wherein the bulkhead connector includes an elongated body having an external thread and a securing nut that can be threadedly moved with respect to a backing nut fixed to the elongated body.

15. A method of disinfecting an interior compartment of a safety cabinet, the safety cabinet including an enclosure and at least one door, the enclosure including an inner shell and an outer shell in a double walled configuration, the inner shell defining an interior compartment and a compartment opening, the interior compartment being accessible via the compartment opening, and the at least one door being rotatably mounted to the enclosure and moveable over a range of travel between an open position and a closed position, the at least one door adapted to occlude the compartment opening of the enclosure when the at least one door is in the closed position, the method comprising:

electrically connecting an interior lighting system disposed in the interior compartment to an external electrical component via an electrical connection disposed through the inner shell and the outer shell of the enclosure and configured to isolate the interior compartment from an exterior environment, the interior lighting system including at least one ultraviolet light source;

attaching the at least one ultraviolet light source to a shelf adjustably mounted to the enclosure within the interior compartment in one of a range of indexed vertical positions;

removably connecting the at least one ultraviolet light source to the external electrical component via an electrical connector mounted to the shelf and electrically connected to the at least one light source and to a conductive strip mounted to the enclosure, the conductive strip being disposed along a vertical axis and including a plurality of sockets disposed over the range of indexed vertical positions, and the electrical connector removably connected to the conductive strip via a respective one of a plurality of sockets of the conductive strip;

occluding the compartment opening by moving each of the at least one door to the closed position; and activating, for a predetermined period of time sufficient to reduce at least one of a microorganism and a pathogen disposed within the interior compartment, the at least one ultraviolet light source of the interior lighting system.

16. The method of claim 15, further comprising:
interrupting a supply of power to the interior lighting system when the at least one door is moved from the closed position to an open position.

17. The method of claim 15, further comprising:
storing an item in the interior compartment of the safety cabinet;
wherein the at least one ultraviolet light source is activated after the item is stored in the interior compartment.

18. A safety cabinet comprising:
an enclosure defining an interior compartment and a compartment opening, the interior compartment being accessible via the compartment opening;
a door being rotatably mounted to the enclosure and moveable over a range of travel between an open position and a closed position, the door adapted to cover at least a portion of the compartment opening of the enclosure when the door is in the closed position;
an interior lighting system including at least one light source disposed in the interior compartment;
a shelf disposed in the interior compartment, wherein the at least one light source is attached to the shelf; and
an electrical connection conductively connected to the interior lighting system, the electrical connection arranged with the enclosure and configured to be electrically connected to an external electrical component such that the interior compartment is isolated from an exterior environment via the electrical connection;
wherein the shelf includes an electrical connector conductively connected to the at least one light source and to the electrical connection.

19. The safety cabinet of claim 18, wherein the shelf is configured to be adjustably mounted to the enclosure over a range of vertical positions, the electrical connection includes a conductive strip mounted to the enclosure and disposed along a vertical axis and including a plurality of sockets disposed over a range of indexed positions along the vertical axis, the electrical connector configured to be removably connected to the conductive strip via a respective one of the plurality of sockets over a range of vertical positions of the shelf along the vertical axis.

20. The safety cabinet of claim 18, wherein the at least one light source is located on an underside of the shelf.

21. The safety cabinet of claim 20, wherein the at least one light source is located on a forward edge of the shelf such that light emitted from the at least one light source id directed toward a rear of the enclosure.

* * * * *